US006211243B1

(12) United States Patent
Johnson

(10) Patent No.: US 6,211,243 B1
(45) Date of Patent: Apr. 3, 2001

(54) METHODS FOR TREATING COLD SORES WITH ANTI-INFECTIVE COMPOSITIONS

(76) Inventor: B. Ron Johnson, 4061 Canyon View Pl., Sandy, UT (US) 84092

( * ) Notice: Subject to any disclaimer, the term of this patent is extended or adjusted under 35 U.S.C. 154(b) by 0 days.

(21) Appl. No.: 09/401,076

(22) Filed: Sep. 22, 1999

(51) Int. Cl.⁷ .................. A61K 31/155; A61K 31/045; A61K 31/24
(52) U.S. Cl. .................. 514/634; 514/724; 514/535
(58) Field of Search .................. 514/634, 724, 514/535

(56) References Cited

U.S. PATENT DOCUMENTS

| | | |
|---|---|---|
| 1,822,566 | 9/1931 | Davies . |
| 3,369,543 | 2/1968 | Ronco .................. 128/269 |
| 4,183,684 | 1/1980 | Avery, Jr. .................. 401/133 |
| 4,262,007 | * 4/1981 | Sherrill .................. 424/274 |
| 4,390,539 | * 6/1983 | Sherrill .................. 424/251 |
| 4,394,381 | 7/1983 | Sherrill .................. 424/274 |
| 4,486,450 | 12/1984 | Bernstein . |
| 4,507,281 | 3/1985 | Asculai et al. .................. 424/85 |
| 4,661,354 | 4/1987 | Finnerty .................. 424/145 |
| 4,822,605 | 4/1989 | Powell .................. 424/85.2 |
| 4,828,542 | 5/1989 | Hermann .................. 604/3 |
| 4,875,602 | 10/1989 | Chickering et al. .................. 222/187 |
| 4,887,994 | 12/1989 | Bedford .................. 601/1 |
| 4,895,727 | 1/1990 | Allen .................. 424/642 |
| 4,929,442 | 5/1990 | Powell .................. 424/85.2 |
| 4,952,204 | 8/1990 | Korteweg .................. 604/1 |
| 4,957,734 | 9/1990 | Miller .................. 424/85.7 |
| 4,975,217 | 12/1990 | Brown-Skrobot et al. .................. 252/107 |
| 5,016,651 | 5/1991 | Stalcup et al. .................. 128/898 |
| 5,036,095 | 7/1991 | Andermann .................. 514/389 |
| 5,137,724 | 8/1992 | Balzarini et al. .................. 424/400 |
| 5,198,217 | 3/1993 | Vedros .................. 424/195.1 |
| 5,387,611 | 2/1995 | Rubinstein . |
| 5,405,602 | 4/1995 | Simmons et al. .................. 424/47 |
| 5,439,685 | 8/1995 | Augros .................. 424/430 |
| 5,503,853 | 4/1996 | Bollen et al. .................. 424/607 |
| 5,527,534 | 6/1996 | Myhling .................. 424/430 |
| 5,631,245 | 5/1997 | Drube .................. 514/62 |
| 5,637,307 | 6/1997 | Simmons et al. .................. 424/405 |
| 5,661,170 | 8/1997 | Chodosh .................. 514/390 |
| 5,678,273 | 10/1997 | Porcelli . |
| 5,704,906 | 1/1998 | Fox .................. 604/1 |
| 5,709,866 | 1/1998 | Booras et al. .................. 424/400 |
| 5,712,257 | 1/1998 | Carter .................. 514/44 |
| 5,725,875 | 3/1998 | Noll et al. .................. 424/445 |
| 5,753,270 | 5/1998 | Beauchamp et al. .................. 424/667 |
| 5,762,940 | 6/1998 | Bourbon et al. .................. 424/217.1 |
| 5,767,163 | 6/1998 | Kundsin . |
| 5,827,870 | 10/1998 | Chodosh .................. 514/390 |
| 5,906,814 | 5/1999 | Epstein . |

FOREIGN PATENT DOCUMENTS

| | | |
|---|---|---|
| 2143136 | 8/1996 | (CA) . |
| 0 181 184 | 5/1986 | (EP) . |
| 0 190 797 | 8/1986 | (EP) . |
| 2 700 698 | 7/1994 | (FR) . |
| 1 479 480 | 7/1977 | (GB) . |
| WO 98/11778 | 3/1998 | (WO) .................. A01N/33/12 |
| WO 98/42188 | 10/1998 | (WO) .................. A01N/33/12 |
| WO 99/08713 | 2/1999 | (WO) . |

OTHER PUBLICATIONS

*AHFS Drug Information*, pp. 3107–3108, 1999.
Berti, et al., Transcutaneous Drug Delivery: A Practical Review, *Mayo Clin. Proc.*, vol. 70, pp. 581–586, Jun. 1995.
Choi, et al., The Pretreatment Effect of Chemical Skin Penetration Enhancers in Transdermal Drug Delivery Using Iontophoresis, *Skin Pharmacol. Appl. Skin Physiol.*, pp. 326–335, 1999.
Comfort et al., Enhanced Transport in a Therapeutic Transdermal System, *Biomaterials*, vol. 11, No. 9, pp. 729–733, Nov. 1990.
Fang et al., Development and Evaluation on Transdermal Delivery of Enoxacin Via Chemical Enhancers and Physical Iontophoresis, *Journal of Controlled Release*, vol. 54, pp. 293–304, 1998.
Fang et al., Evaluation of Transdermal Iontophoresis of Enoxacin From Polymer Formulations: In Vitro Skin Permeation and In Vivo Microdialysis Using Wistar Rat as an Animal Model, *International Journal of Pharmaceutics 180*, pp. 137–149, 1999.
Gismondo, et al., Efficacia Antimicrobica e Sporicida di Varie Soluzioni Disinfettanti, *Minerva Medica*, (Italy) vol. 86, pp. 21–32, Jan.–Feb. 1995 (English translation attached: Antimicrobial and Sporicidal Efficacy of Some Disinfectant Solutions).
James Alexander Corporation flyer, *Medicaine® Sting and Bite Relief Formula Flyer*, 1997.
James Alexander Corporation flyer, *Medicaine® Topical Antiseptic,*, 1997.
James Alexander Corporation flyer, *Unit Dose Swabs*, 1997.
Jin et al., Effect of Application Volume of Ethanol–Isopropyl Myristate Mixed Solvent System on Permeation of Zidovudine and Probenecid Through Rat Skin, *Drug Development and Industrial Pharmacy*, vol. 26 No. 2, pp. 193–198, 2000.

(List continued on next page.)

*Primary Examiner*—Kevin E. Weddington
(74) *Attorney, Agent, or Firm*—Workman Nydegger Seeley

(57) ABSTRACT

The present invention relates to a method of treated disordered epithelial tissues such as cold sores and other complications resulting from disorders such as herpes, and the like. The inventive method combines an anti-infective and/or antimicrobial active agent in a carrier, with vigorous agitation of the disordered epithelial tissue for topical treatment thereof under such conditions sufficient to achieve clinically discernable improvement of the disordered epithelial tissue. The preferred anti-infective and/or antimicrobial active agent is an organohalide such as a quaternary ammonium compound, preferably benzalkonium chloride. The inventive method may be used also in connection with a preferred applicator configuration.

51 Claims, 6 Drawing Sheets

OTHER PUBLICATIONS

Johnson, et al., Supergistic Effects of Chemical Enhancers and Therapeutic Ultrasound on Transdermal Drug Delivery, *Journal of Pharmaceutical Sciences*, vol. 85, No. 7, pp. 670–679, Jul. 1996.

Kanikkannan, et al., Structure–Activity Relationship of Chemical Penetration Enhancers in Transdermal Drug Delivery, Current Medicinal Chemistry, vol. 7, No. 6, pp. 593–608, 2000.

Martindale, The Extra Pharmacopoeia, Benzethonium Chloride/Benzyl Alcohol, p. 1119, Royal Pharmaceutical Society, 1996.

Martindale, The Extra Pharmacopoeia, Disinfectants and Preservatives, pp. 1114–1116, Royal Pharmaceutical Society, 1996.

Martindale, The Extra Pharmacopoeia, Ethyl Hydroxybenxoate/Magenta, p. 1137, Royal Pharmaceutical Society, 1996.

Martindale, The Extra Pharmacopoeia, Local Anesthetics, p. 1317, 1320–1321, Royal Pharmaceutical Society, 1996.

The Merck Index, An Encyclopedia of Chemicals, drugs, and Biologicals, Twelfth Edition, pp. 177 and 180, 1996.

Meyler's Side Effects of Drugs, An Encyclopedia of Adverse Reactions and Interactions, Antiseptic Drugs and Disinfectants, Chapter 24, pp. 643–655 and 664–665, 1996.

Sanofi Pharmaceuticals, Inc., Zephiran® Chloride, Brand of Benzalkonium Chloride, 1997.

Williams, et al., Skin Absorption Enhancers, *Critical Reviews in Therapeutic Drug Carrier Systems*, 9(3,4), pp. 305–353, 1992.

Wu et al., In Vitro Effect of Penetration Enhancers on Sodium Nonivamide Acetate in Rat Skin, *Biol. Pharm. Bull.*, vol. 18, No. 12, pp. 1790–1792, 1995.

Physicians Desk Reference for Non–Prescription Durgs, Product Information, pp. 643, 644, 649, 503 507, and reference pages to Bactine, and Tanac, 1998.

Winthrop Laboratories, Zephiran® Chloride, Informational Brochure, Jul., 1980.

Encyclopedia Brittanica, Inc., Definitions of Skin and Skin, Diseases of, pp. 603–609, 1970.

DentalDots® What are they?, located at "http://www.dentaldots.com/whatsadot.htm," p. 1, web page dated Jul. 14, 1999.

ViraMedx/Really Fast Relief for Herpes Related Outbreaks, located at "http://www.viramedx.com/," 1 page, web page dated Jun. 28, 1999.

Cold Sores Healed in Less than 24 Hours Report Says, located at "http://www.viramedx.com/news01.htm," 2 pages, web page dated Jun. 28, 1999.

Comparison of Zovirax, Valtrex, Famvir and VirMedx, located at "http://www.viramedx.com/compare.htm," 1 page, web page dated Jun. 28, 1999.

Herpes Treatment That Works on Genital Herpes Too, located at "http://www.viramedx.com/about.htm," 1 page, web page dated Jun. 28, 1999.

Herpes Treatment Shows Promise Against Genital Herpes, located at "http://viramedx.com/study.htm," 1 page, web page dated Jun. 28, 1999.

Results Against Clinical Strains of Herpes Simplex Virus, located at "http://www.ciramedx.com/labdata.htm," 1 page, web page dated Jun. 28, 1999.

8 Year Study to Determine Effectiveness Against Herpes, located at "http://viramedx.com/clinicaldata.htm," 1 page, web page dated Jun. 28, 1999.

8 Year Study to Determine Effectiveness Against Herpes, located at "http://www.ciramedx.com/results.htm," 5 pages, web page dated Jun. 28, 1999.

8 Year Study to Determine Effectiveness Against Herpes, located at "http://www.viramedx.com/clinicalsum.htm," 2 pages, web page dated Jun. 28, 1999.

Sigma Product Information Sheet, *Benzalkonium Chloride*, located at http://www.sigma.sial.com/sigma/proddata/b1383.htm.

ViraMedix, Antiviral Activity of Viracea® Against Acyclovir Resistant Strains of Herpes Simplex Virus (HSV), located at "http://www.herpescontrol.com/acyresist.htm," by K.D. Thompson et al., The University of Chicago and Meryx Pharmaceutical, Chicago, Il (study results found at http://www.herpescontrol.com/figure3.htm).

ViraMedix News Release, Announcing the First OTC Treatment Proven to "Kill" the Herpes Virus that Causes Cold Sores, Fever Blisters and Related Outbreaks, Healing the Outbreak in Usually Less Than 24 Hours/Timely Introduction in Light of Recent News of the Spread of Herpes Caused Outbreaks and Just in Time for the Summer Sun Caused Outbreaks of Cold Sores, located at "http://www.herpescontrol.com/news01.htm.".

Study Results, Testimonials, located at "http://www.herpescontrol.com/results.htm".

\* cited by examiner

METHODS FOR TREATING COLD SORES WITH ANTI-INFECTIVE COMPOSITIONS

BACKGROUND OF THE INVENTION

1. The Field of the Invention

The present invention relates to systems and methods for treating disordered tissue with anti-infective compositions especially antiviral and antimicrobial compositions. More particularly, the treatment compositions include quaternary amine medicament compounds or organochlorides. The present invention provides a novel combination of treatment compositions and modes of applying them to treat tissue disorders, particularly epithelial tissue disorders such as herpes infections.

2. The Relevant Technology

Tissue disorders, particularly those which impact epithelial tissue such as Herpes Simplex types I and II, candida albicans, acne, psoriasis, eczema, seborrhea, dermatitis, and pink eye are common and are often difficult to treat symptoms. Such disorders are more likely to develop in people living with compromised sanitary conditions, the elderly, and the chronically ill. Others susceptible to such disorders include workers in health care, agricultural workers, chemical industry workers, individuals working with industrial cleaners, and painters, where chronic exposure to chemicals, pathogens, and unsanitary conditions tend to weaken and irritate epithelial tissue.

Herpes simplex virus (HSV) and Herpes Zoraster, commonly referred to as "herpes virus" or "herpes," is an infectious disease which has reached crisis proportions nationally with estimated numbers of infected people at 70%–80% of U.S. population as reported by the American Social Health Association (ASHA) and growing annually by 500,000 people or more. There are two common types of herpes: herpes simplex virus I (HSV 1) and herpes simplex virus 2 (HSV 2).

Herpes enters the human body through minuscule breaks in the epidermal tissue usually by contact with an infected host and is marked by eruption of one or more vesicles, usually in groups, following an incubation period of approximately four to ten days. Typically the course of the infectious outbreak initiates with the prodromal stage; advancing to vesicular eruption; followed by: ulceration; coalescing; resolution; and the latency period. The outbreak can last for several weeks and on average lasts two to three weeks. In some immune compromised individuals, the outbreak can last for months. The vesicles can appear anywhere on epithelial tissues including the skin or mucosa, typically appearing on the lips as cold sores, glands, oral mucosa, conjunctiva and cornea, genitalia, anal mucosa and peri-anal tissue.

Herpes symptoms include: inguinal swelling, pain, fever, malaise, headaches, muscle aches, and swollen glands. Some individuals with oral herpes which impacts the trigeminal nerve, have excruciating facial pain, difficulty swallowing, eating and facial swelling. Individuals with the herpes which impacts the sacral nerve have severe upper leg pain, swelling, and great difficulty walking.

Herpes simplex virus (HSV) infection is recurring, residing in the nerve ganglia, then recurring due to some, as yet unknown, stimulus. Recurrent herpetic infections can be precipitated by almost anything, including: overexposure to sunlight; nutritional deficiencies; stress; menstruation; immunosuppression; certain foods; drugs; febrile illness; etc.

Herpes infections pose very serious health threats often causing: blindness; increased cancer risk of the cervix; aseptic meningitis and encephalitis; neonatal deaths; viremia; the spread of the human immunodeficiency virus (HIV); etc. The devastating effects of this disease, go well beyond the medical scope of human suffering; HSV is responsible for serious psychological and emotional distress as well as substantial economic loss.

Various treatments for herpes have been proposed and have included topical application of such agents as povidone-iodine, idoxuridine, trifluorothyidine, or acyclovir. Such treatments have met with varying degrees of success. Most prior treatments have proven disappointing. Acyclovir, an acyclic nucleoside, is taken orally for systemic treatment of HSV. Acyclovir is somewhat effective in inhibiting the activity of several herpes viruses. However, acyclovir is only successful in interrupting the replication of the virus and is used to treat infectious outbreak systemically. Nothing to date has proven really effective topically. Strains resistant to acyclovir have been reported. Individuals with Auto Immune Deficiency Syndrome (AIDS) are seriously immune-compromised and suffer especially debilitating outbreaks of HSV. Additionally, AIDS individuals may carry acyclovir resistant strains of HSV, which can make acyclovir ineffective for these individuals. It is, therefore, of utmost importance to develop a safe and successful medical treatment to overcome the very serious problems of herpes virus.

Biologically active antiviral and microbial compositions have been met with marginal success when administered topically for tissue disorders. Such compositions have been applied as gels, creams, lotions, oils, ointments, pastes, tinctures, emulsions, and colloidal suspensions. Most of the compositions are oil-based to ensure that the composition has sufficient viscosity and/or tackiness to remain on the surface of the skin. In fact, such compositions are generally absorbed into clothing more than into the skin due to a relatively slow epidermal penetration rate. Even when applied to patients and time is available for the compositions to penetrate, they often were not sufficiently effective for one reason or another to substantially assist them in clearing up the disorder.

Many efforts have been undertaken to remedy the inadequate results of topically administered compositions having antiviral and antimicrobial qualities. The therapeutic effects of such compositions depend upon the specific active agent and the method of application. Many compositions of the prior art contain ingredients that may provide symptomatic relief of pain and itching, but none are claimed to be effective against Herpes infection except the drug, acyclovir, which is purported to have some topical efficacy. Additionally, most compositions intended to treat such disorders do not effectively treat the discomfort and the disease symptoms, let alone cure the disorder or put it into a significant remission.

Examples of conventional application methods and compositions are provided in WO 98/42188 and in WO 98/11778 by Squires, both of which are hereby incorporated by reference. In WO 98/42188 at page 9, lines 12–18 and in WO 98/11778 at page 5, lines 22–30, it is stated that the composition is applied by "spraying, dabbing, dusting, swabbing, sponging, brushing, pouring, dispensing, covering or heavily coating." The stated objective of these techniques for applying the composition is to insure that the composition remains on the infected area. Like other conventional treatment compositions, the composition has a viscosity and/or tackiness which enables it to remain on the surface of the infected area. A portion of such compositions may eventually penetrate beyond the surface of the disordered tissue such as the outer surface of skin or a lip, however, the viscosity of the composition combined with the application technique prevents such compositions from achieving effective penetration.

Another example of conventional application methods and compositions is provided in U.S. Pat. No. 5,753,270 issued to Beauchamp et al., which is also incorporated by reference. U.S. Pat. No. 5,732,270 discloses a composition which includes: (a) an antiseptic and/or anesthetic compound which is (i) a terpene such as menthol or eucalyptol, (ii) a phenolic compound such as thymol, or (iii) an alcohol such as menthol; (b) a quaternary ammonium antiseptic compound such as benzethonium chloride; and (c) an antiseptic compound containing iodine, salts thereof and/or complexes thereof dissolved in an organic skin penetrating solvent such as a mixture of water and acetone. The methodology is described in the examples provided at columns 5–7 as involving the liberal application of the composition to the afflicted area in a sequence such as 3 to 4 applications over a one minute period which is then repeated every 3 minutes over a 10 minute period. The entire procedure is then repeated after approximately ½ to 1 hour for 2 to 3 hours or until activity is stopped in healing is evident. The use of a cotton swab is mentioned at column 6, lines 10–11 for applying the composition.

Although it is mentioned in U.S. Pat. No. 5,753,270 at column 3, lines 44–49 that the formulations may be prepared as a gel, cream, a lotion, an ointment, or a paste the preferred embodiment appears to be a solution having an aqueous solvent system. It is noted at column 3, lines 6–9 that although use of water and acetone as a solvent is preferred such a solvent is not considered essential to the overall synergistic action of the formulation. In any event, the formulation appears not to rely on either its viscosity or tackiness to ensure that the formation is maintained on the surface of the afflicted area as do most conventional Rather the methodology involves the very frequent reapplication of the formulation to the afflicted area. Some of the formulation may be absorbed into the skin, however, a significant portion is likely rapidly evaporated due to the high content of water and acetone.

The active agents disclosed in U.S. Pat. No. 5,753,270 which are discussed above include at least one compound which is an antiseptic and/or an anesthetic. The primary examples of such compounds: menthol, eucalyptol, and thymol are either obtained from natural sources such as naturally occurring oils or are derived from such oils. Eucalyptol is described as being an essential oil and a terpene ether. Thymol is derived from thyme oil or other oils. Menthol is obtained from peppermint oil or other oils. Other suitable compounds are also recited in the claims as including: eugenol, camphor, hexetidine or anethol. While the basis for inclusion of hexetidine in this grouping is not clear, the other chemicals are also obtained from natural sources or are derived therefrom. Eugenol is obtained by extraction of clove oil and then chemical modification. Camphor is a ketone which occurs naturally in the wood of the camphor tree. Anethol is derived from anise or fennel oils. While these compounds are useful, particularly as antifungal agents, it is doubtful that they assist in penetrating the afflicted tissue and may in fact retard or enhance the skin's natural resistance to penetration.

In conclusion, significant medical research in this field of endeavor has been focused on developing compositions used for treating affected tissues and yet compositions which provide rapid relief to these ailments are still needed. It would therefore be an improvement in the art to provide a method of treating tissue disorders such as epithelial tissue disorders that overcome the problems of the prior art.

Such methods and systems of application are taught and claimed herein.

SUMMARY AND OBJECTS OF THE INVENTION

The present invention relates to methods and systems for treating disordered tissue. The system and methods involve the use of an applicator to apply a treatment composition comprising an anti-infective active agent in a carrier. The method may include vigorously agitating the disordered tissue treatment site with the applicator under conditions which are sufficient to enable the anti-infective active agent to rapidly penetrate the disordered tissue.

The present invention relates to the treatment of tissue disorders such as infections, particularly herpes related cold sores or other herpes disordered tissue. Throughout this disclosure, use of the term "disordered tissue" or "afflicted tissue", is understood to represent all tissue which has been affected by disorders such as, cold sores, all Herpes, candida albicans, acne, psoriasis, eczema, seborrhea, dermatitis, pink eye, shingles, and other predominantly viral disorders. Microbial and fungal infections are also types disordered tissues. Additionally, disordered tissue includes tissue which has been infected by venom as results from snake and spider bites, particularly venom infections from Brown Recluse spiders and Black Widow spiders.

It has been found that the therapeutic irritation of disordered tissue with a preferred treatment composition and the optional use of an applicator, stimulates rapid immunological attack and makes the composition and therapeutic irritation synergistically more effective. After the therapeutic irritation of the disordered tissue through vigorous rubbing and/or pressure, the treatment composition penetrates into the disordered tissue to enable the anti-infective active agent or agents to become chemically active much more deeply within the disordered tissue as compared to conventional application techniques.

In addition to the anti-infective active agent or agents, the composition also includes a carrier such as an alcohol. Oil and fatty carrier substances are preferably not added to the composition. Although various compositions have been applied to disordered tissue, the inventive methods and systems of vigorous irritation of the disordered tissue in connection with a preferred composition has extraordinary therapeutic effects. Consequently, the inventive compositions and methods of application with vigorous irritation of disordered tissue provide effective methods of treatment.

The inventive systems utilize an applicator to vigorously irritate disordered tissue to convey the inventive composition into the disordered tissue. The applicators allow the patient or a health professional to vigorously irritate the disordered tissue without cross-contamination from a dirty finger or the like. A finger may be used, of course, but it lacks the advantages of a sterile applicator, the absorbability of an applicator tip and the ability to irritate the skin surface in the desired manner. The applicator has the added advantage of directing focused pressure into the disordered tissue while the active compounds are expressed from the applicator into the disordered tissue. The combined effect of vigorous irritation of the disordered tissue and the administration of the inventive treatment compositions has the remarkable result of surprising therapeutic effects. Note that oils on the finger may react with the active agent and lessen its impact in the disordered tissue. For this same reason, moisturizing lotions should preferably not be applied to the treatment area after application of the treatment composition.

It is therefore an object of the present invention to provide a method for treating disordered tissue such as disordered portions of skin and mucous membranes. It is therefore an object of one embodiment of the present invention to provide a system for the treatment of epithelial tissue disorders that includes a preferred biologically anti-infective active composition and an applicator in connection with vigorous irritation of the disorder site.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
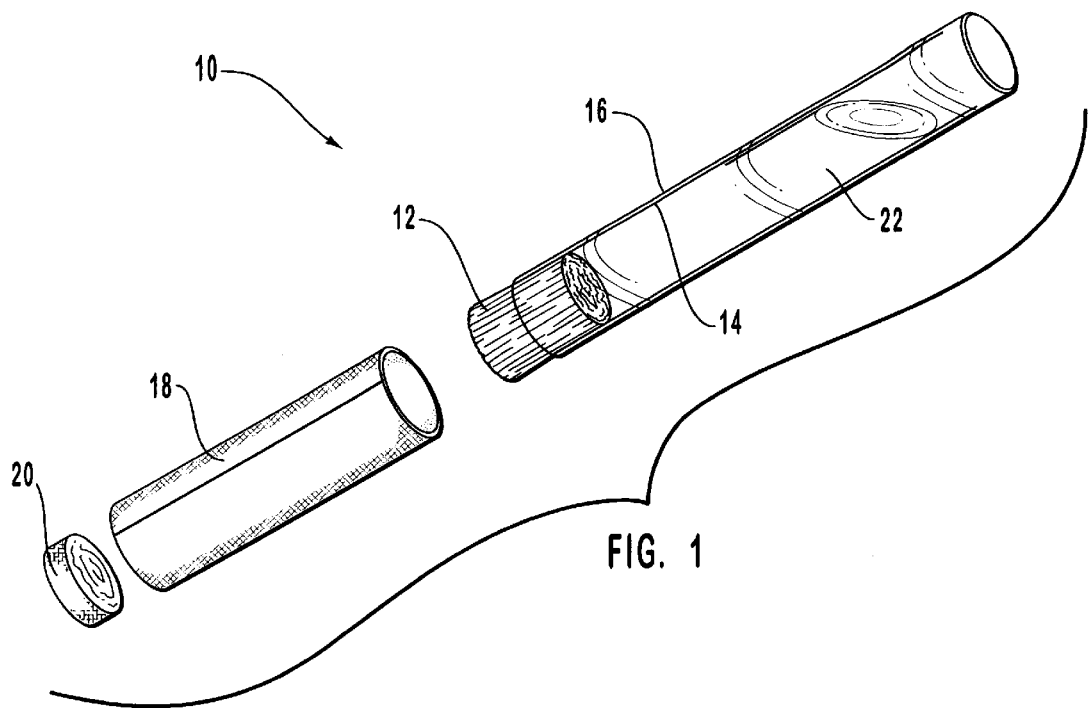
FIG. 1 is an exploded perspective view of a preferred applicator that contains the treatment composition.

The present invention relates to methods and system for treating disordered tissue through the combined use of a treatment composition and the vigorous irritation of the disordered tissue site with the optional assistance of an applicator. The present invention provides compositions that are any one or all of antiviral, antimicrobial, antifungal, or antivenomous. The present invention also provides a method of their application in a manner that is remarkably efficacious in causing the compositions to penetrate into disordered tissue and to preferably stimulate the immune responses. The combination of the delivery of anti-infective compositions and the stimulation of the immune responses caused by the vigorous irritation of the disordered tissue, presents a surprising result in the treatment of epithelial tissue disorders.

Hereinbelow is a discussion of what is meant by vigorous irritation of disordered tissue, followed by a detailed description of the treatment composition. The description of the treatment composition is followed by a detailed description of several embodiments of applicators. FIGS. 1–5 depict a preferred applicator. Other embodiments of applicators are shown in FIGS. 7–10. FIG. 6 depicts a cross-sectional view of skin.

The phrase "vigorous agitation" means that the skin is irritated in a manner that allows the inventive compositions to penetrate below the surface of the skin, preferably to a nerve ending. As described in more detail hereinbelow, such vigorous agitation is achieved through either apply an appropriate amount of pressure for an adequate period of time and/or appropriate rubbing for an adequate period of time. Vigorous agitation is preferably a combination of both adequate pressure and rubbing.

A suggested theory for the effectiveness which results from vigorously agitating the disordered tissue is set forth below. However, it should be understood that the objective in vigorously agitating the disordered tissue includes moving the tissue to better enable the treatment composition to physically move through the layers of the disordered tissue by moving the cells and fluids in the disordered tissue. Also, another objective of vigorous agitation is to stimulate the immune responses.

Vigorous agitation achieved through applying appropriate pressure may be understood to be an amount of pressure such that, where tissue overlies bone, the tissue is depressed to be firmly against the bone. Similarly, if the disordered portion of the tissue is adjacent to teeth or gums such as the skin around the mouth, then the disordered tissue is sufficiently compressed due to the pressure that the pressure is felt on the opposing surfaces within the mouth. Additionally, if disordered tissue located around a patient's lip is also opposite the patient's gums then pressure applied to the disordered tissue would also be felt at the portion of the patient's gums opposite the disordered tissue through the lip or cheek.

Vigorous agitation achieved though rubbing involves a steady back and forth motion applied with an applicator onto the disordered tissue. As described in greater detail in reference to the applicator, the applicator is preferably configured to provide a relatively uniform abrasive action. The oscillation rate of the back and forth motion depends on several factors such as the amount of pressure being simultaneously applied and the condition of the disordered tissue. So in some instances the oscillation rate may be only 1 stroke per second or less while in other circumstances the oscillation rate may range from about 1 strokes per second to about 10 strokes per second. More typically, however, the oscillation rate is in a range from about 2 strokes per second to about 6 strokes per second and is most typically in a range from about 3 strokes per second to about 4 strokes per second. Note that the portion of the applicator used to rub the disordered tissue preferably has a size in a range from about 50% to about 200% the size of the disordered tissue treatment site.

The length of time that vigorous agitation of this type may be sustained upon a disordered tissue treatment site may vary according to the individual, the size of the applicator surface in relation to the size of the disordered tissue to be agitated, the amount of pressure applied as defined above and the oscillation rate of the rubbing. Typically, the vigorous agitation is maintained for at least 1 second and is more typically maintained for a period of time in a range from about 3 seconds to about 1 minute. Vigorous agitation is most typically maintained for a period of time in a range from about 5 seconds to about 15 seconds.

It is counterintuitive to vigorously agitate disordered tissue such as a cold sore as the disordered tissue already hurts so one inherently desires to avoid even contacting such sensitive disordered tissue. However, patients are likely to be more tolerant of any pain which may result from vigorous agitation when bolstered by knowledge that vigorous agitation significantly enhances the ability of the treatment compositions disclosed herein to effectively penetrate disordered tissue.

Vigorous agitation need not necessarily be painful, although, vigorous agitation may also be understood to mean that discomfort is felt by the patient beyond nominal dabbing of the disordered tissue as with other treatments that call for gentle application to the disordered tissue. Before a cold sore has erupted, and is in the prodromal stage or vesicular stage such that at most there is merely a vistule, it may not be painful to vigorously agitate the disordered tissue. However, when vigorously agitating disordered tissue which is in an erupted stage, the agitation may be sufficient to cause sharp pain and bleeding.

As indicated above, the vigorous agitation can also be defined by contrasting it with nominal dabbing of the disordered tissue which involves the mere application of a treatment composition. The same is likewise true for other application techniques such as swabbing, sponging, and brushing merely to ensure that a treatment composition is applied. Dabbing and other application techniques do not involve pressing hard enough such that the disordered tissue is compressed against a bone or such that pressure is felt as a surface in the mouth opposite the disordered tissue is pressed against teeth or gums. Mere application of a treatment composition such as nominal dabbing of the disordered tissue does not cause bleeding of the disordered tissue, for example, if it is a cold sore in an erupted stage.

Despite a patient's desire to enable disordered tissue to return to normal some patients are also likely to adjust the amount of pressure applied or the rate of rubbing in order to experience minimal pain. However, as indicated above, it is not necessary for a patient to feel pain in order for the treatment composition to be delivered with vigorous agitation. The objective is to move the tissue somehow either through compressing the tissue through the application of an appropriate amount of pressure as discussed above for an adequate period of time and/or by rubbing the tissue in manner such that tissue is moved around for an adequate period of time for the treatment composition to penetrate such that it does not remain on the surface. More particularly, the treatment composition is preferably absorbed into the disordered tissue to such an extent that within several minutes after application the composition can no longer be seen. More preferably, the composition is not visibly detectable within 2 minutes after being applied and is most preferably not visibly detectable within 1 minute after being applied. Note that the content of the composition has different formulations, however, in the preferred embodiment there is no residue remaining after the composition has been applied and absorbed which is visibly detectable.

As indicated above, the treatment composition preferably penetrates through the skin to a nerve ending or causes a penetration sensation at the nerve ending. After the composition is delivered with simultaneous agitation, the penetration or the penetration sensation preferably occurs within about one minute. The penetration or penetration sensation to a nerve ending is more preferably achieved in about 30 seconds and most preferably in less than about 10 seconds. In more serious cases when the disordered tissue represents an extensive amount, several treatments may be used instead of a single, primary treatment. Note that when several treatments are used instead of a single, primary treatment, it is preferable to use a clean and sterile applicator for each repeated treatment.

The penetration into disordered tissue enabled by the vigorous agitation is further enhanced through the use of treatment compositions that have particular properties. The treatment compositions include at least a biologically active agent and a carrier. The biologically active agent is able to be effective in stopping tissue disorders such as cold sores, as the carrier is selected to optimally enable the treatment composition to penetrate. The biologically active agents suitable for use in the treatment compositions are set forth hereinbelow and then the carriers are described. Other optional components are also described.

The biologically active agents or anti-infective agents included in the anti-infective treatment compositions are preferably anti-infective organohalides, especially anti-viral organohalides. Benzalkonium chloride is the preferred organohalide. However, other organohalides or quaternary ammonium compounds may be used as the active agents in the compositions. Other active agents that are organohalides may include organo-bromides and organo-iodides. Preferably, the organohalides have an alkyl group attached thereto such as a simple $C_nH_{2n+1}$ chain, where n is in a range from 1 to about 50.

The chemical structure of benzalkonium chloride is shown below:

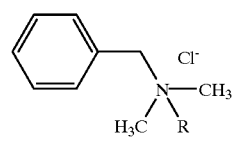

wherein R=$C_8H_{17}$ to $C_{18}H_{37}$. As shown, benzalkonium chloride includes a benzene ring and a nitrogen constituent adjacent the ring. A carbon atom is disposed between the nitrogen constituent and the benzene ring. Two methyl groups and an R group of varying size extend from the nitrogen atom.

These anti-infective agents, particularly benzalkonium chloride, are highly effective in limiting the source of infections and other complications related to disordered tissue. Also, these anti-infective agents destroy or eliminate toxins caused by substances such as viruses. Note that the toxins and their sources are rapidly eliminated to result in almost immediate pain relief.

While the active agents include organohalides, most suitable organohalides are organochlorides. Benzalkonium bromide is an example of a suitable organohalide which is not an organochloride. Benzalkonium bromide has the structure of benzalkonium chloride with the difference that the chlorine is substituted with a bromine radical. Another example of a suitable organohalide which is not an organochloride is cetyl trimethylammonium bromide.

Other organochlorides which have anti-infective properties and are suitable for use as the anti-infective organochloride in the treatment composition include: benzethonium chloride, methyl benzethonium chloride, cetyl pyridinium chloride, chloroxylenol, hexachlorophene, triclosan, chlorhexidine. Note that some of the above organochlorides are not suitable for all purposes. For example, benzethonium chloride cannot be used in a manner which would enable it to be ingested in a toxic quantity as it is potentially toxic if ingested. Similarly, the concentration of benzalkonium chloride must not be excessively high.

Additional examples of other organochlorides which may be suitable, more particularly quaternary ammonium chlorides having 6–18 carbons, include: alkylbenzyldimethylammonium chloride, alkyldimethyl/ethylbenzylammonium chloride, n-alkyldimethylbenzylammonium chloride, diisobutylphenoxyethoxyethyldimethylbenzylammonium chloride, N—($C_{12}C_{14}C_{16}$) dimethylbenzylammonium chloride, didecyldimethylammonium chloride, dioctyldimethylammonium chloride, dialkyldimethylammonium chloride, dialkylmethylbenzylammonium chloride, octyldecyldimethylammonium chloride, dimethylbenzylammonium chloride, laurrydimethylbenzylammonium chloride, o-benzyl-p-chlorophenol, dideryldimethylammonium chloride, dioctyldimethylammonium chloride, alkyl ($C_{14}C_{12}C_{16}$) dimethylbenzylammonium chloride. In addition to these organochlorides, other known antimicrobial agents may also be used as the active agent or in combination with the active agents provided above. For example, chemicals which are known to act as an antiviral, antibacterial or antifungal agents such as the antifungal agents disclosed by Chodosh in U.S. Pat. No. 5,661,170 and U.S. Pat. No. 5,827,870, which are hereby incorporated by reference. It is also possible that a chemical such as acyclovir may be effective as an anti-infective agent when delivered with the carriers as disclosed herein combined with vigorous agitation. So in contrast to the conventional understanding that acyclovir is ineffective when topically applied, it may be useful as an anti-infective agent when used as taught herein. Note, however, that acyclovir is not an organohalide and so may not be as easily absorbed into the skin or penetrate as readily.

When the anti-infective agent is benzalkonium chloride, the concentration is preferably in a range from about 0.01% to about 0.5% by volume of the treatment composition, more preferably in a range from about 0.05% to about 0.3% by volume of the treatment composition, and even more preferably in a range from about 0.1% to about 0.2% by volume of the treatment composition. To avoid toxicity, the concentration is less than 0.26% and is most preferably about 0.13% by volume of the treatment composition. Depending on the particular, organohalide or quaternary ammonium chloride, the concentration may vary. For example, the concentration may range from about 0.001% to about 2% by volume of the treatment composition.

For the specialized treatment of the eyes, an eyewash having the active agent is made into a composition with an active agent concentration in the volume range from about 0.001% to about 0.05%. Preferably, the active agent concentration for an eyewash is in the range from about 0.005% to about 0.03%. The specialized treatment of the eyes may also require several treatments instead of a single, primary treatment. Where eye drops are used, according to the inventive method, the composition is deposited onto the eye and the patient closes the eye after the eye has been contacted with composition, and the patient may opt to rub the eyeball through the eyelid to assist in the vigorous irritation of the eye tissue. A subsequent treatment and a series of subsequent treatments may also be carried out on the eyes.

As indicated above, the carrier is a vehicle for the biologically active agent, more particularly the anti-infective active agent. The carrier causes effective wetting of the tissue to be treated and then enables the anti-infective agent to move within this carrier into the disordered tissue.

In one embodiment, the treatment composition consists of only the active agent such as benzalkonium chloride and the carrier. In other embodiments, the treatment composition consists essentially of the active agent and the carrier, however, other components may also be included as described hereinbelow. In any event, the carrier is preferably sufficiently inert with respect to the active agent and any other component present to enable the treatment composition to be stored for long periods of time without deactivating the anti-infective agent, such as 1 year and preferably 2 years.

The carrier has properties which enhance the ability of the treatment composition to penetrate into the disordered epithelial tissue. More particularly, the carrier has a viscosity and/or density which is about the same as water or lower in order to optimally enable the treatment composition to penetrate into the disordered tissue. Using a carrier position having a viscosity which is not greater than that of water is in sharp contrast to conventional compositions which enable the composition to be coated onto afflicted tissue. Accordingly, the treatment compositions specifically exclude formulations which may be considered to be primarily or essentially gels, creams, lotions, oils, ointments, pastes, emulsions, and colloidal suspensions. Note however that small amounts of inert abrasive material may be present in the treatment compositions as discussed hereinbelow. Note also the carrier may include substances which have either a viscosity or density which is more than slightly greater than that of water as long as other substances are also included in the carrier such that the mixture has either a viscosity or density which is about the same as that of water or lower.

The carrier may be formed from a single liquid constituent such as water or an alcohol as described hereinbelow, or from more than one constituent. Although, water alone may be used as the carrier, it is not preferred because other compounds, such as some alcohols, have a tissue penetrating capability that water does not have. The carrier in the treatment composition is also preferably not formed entirely from an alcohol such as isopropyl alcohol or ethyl alcohol, since their use may be more painful in some circumstances. More particularly, when an open sore is part of the disordered tissue, the amount of alcohol or other composition that has a significant tissue penetrating ability may be modified by adding water so as to moderate the amount of discomfort that the patient experiences by the application of the composition to the open sore. Additionally, alcohols such as isopropyl alcohol rapidly evaporate. Further, it may be preferred to use alcohols such as isopropyl alcohol with other constituents such as water due to regulatory issues.

The most preferred carrier is isopropyl alcohol as it is highly effective in penetrating tissue. While not being limited by any particularly theory, it is suggested that isopropyl alcohol opens cells and is not blocked by lipids or lipid layers in the disordered tissue. In addition to isopropyl alcohol, ethanol, and methanol are also suitable carriers. Benzyl alcohol is another preferred alcohol constituent as it also act as a bacteriostat and an anesthetic. Mixtures of the above-mentioned alcohols are also preferred depending upon the application. As indicated above, however, isopropyl alcohol or ethyl alcohol is preferably used in combination with other carrier constituents. For example, as mentioned above water may be added to isopropyl alcohol in order to reduce the pain which may be felt when only isopropyl alcohol is used. Similarly, isopropyl alcohol may be utilized with cetyl alcohol or with a combination of both cetyl alcohol and water to reduce the sensation.

As noted above, the carrier preferably has a tissue-penetrating constituent. It has been noted that the ability of the treatment composition to penetrate disordered tissue is significantly enhanced when at least a portion of the carrier is an alcohol. It is believed that when at least a portion of the carrier is alcohol the carrier has the ability to remove lipids from the tissue.

When the carrier includes water and at least one alcohol, the water is preferably included in a range from about 10 percent to about 50 percent by volume of the carrier. The water content is more preferably in a range from about 20 to about 40 percent by volume of the carrier and is most preferably about 30 percent by volume of the carrier. Although, these ranges of water content are provided based on the volume of water in the carrier, essentially the same water contents apply to the overall treatment composition since the other active agent and any other optional component are typically included in such small amounts.

Other compounds that are preferred as carriers include acetic compounds such as acetone, acetic acid, acetic anhydride, and the like. While some acetic compounds may not be as effective as certain alcohols, particularly isopropyl alcohol, acetone exhibits an effective ability to penetrate tissue. One preferred carrier combination is ethanol and acetone in a ratio of about 70% ethanol by volume of the carrier, preferably 80% ethanol and most preferably about 90% ethanol with 10% acetone by volume of the carrier. As mentioned above with respect to the water content for carriers formed from water and alcohol, the ratios provided for combinations of ethanol and acetone apply also to the treatment composition.

The above carriers may also be combined across class lines. As such, the carriers such as water, alcohols, and acetic compounds may be combined. One example is water, alcohol, and acetone in respective amounts of 30%, 60%, and 10%, by volume of the carrier. Generally speaking, the constituents may be combined in any suitable ratio such as: 1:1:0, 1:2:0, 1:10:0, 1:1:1, 1:2:1, 1:10:1, 1:10:10, and 1:2:10.

As indicated above, the carrier preferably includes alcohol as it is believed that alcohols included in sufficient quantity to act as the carrier may have the quality of removing lipids from the tissue and thereby enabling the active agent to move within the disordered tissue. It is also believed that the ability of the treatment composition to penetrate the disordered tissue is hindered by including components in the composition such as oils or materials which have traditionally been included to enable the composition to be coated onto the surface of the disordered tissue. Examples of such materials include petrolatum which is used in various cold sore treatment compositions. For example, the popular over-the-counter lip ointment sold under the trademark BLISTEX by Blistex Incorporated of Oakbrook, Ill. 60521. The BLISTEX ointment contains allantoin (1%), camphor (0.5%) and phenol (0.5%) in an emollient base with petrolatum, lanolin, menthol, methyl salicylate, and other ingredients. Other widely used ingredients which are included to increase the viscosity or to increase the tackiness includes polyethylene glycol and polypropylene glycol. An example of a product which utilizes polyethylene glycol and polypropylene glycol is a gel sold under the trademark ORAGEL MOUTH AID by Del Laboratories Incorporated of Farmingdale, N.Y. 11735. Other thickeners are taught in U.S. Pat. No. 5,661,170, which was previously incorporated by reference, as including cellulosic materials and waxes. In addition to petrolatum based materials and thickeners, it is also believed that materials which are either obtained from natural sources such as naturally occurring oils present in trees, bushes, plants, etc. or substances which are derived from such oils may also reduce the ability of the treatment composition to penetrate the disordered tissue. Such materials are referred to herein as penetration inhibiting components.

As indicated above, penetration inhibiting components includes chemicals which are petrolatum based substances, materials conventionally utilized as thickeners, naturally occurring oils, substances derived from naturally occurring oils or any other substance which is added primarily to increase the tendency of a treatment composition to remain on the surface of disordered tissue such as a cold sore. Note that while substances such as petrolatum or thickeners are not added individually, a component may be added which includes minute amounts of naturally occurring oils or substances derived from oils obtained from natural sources. So although, the inventive composition is preferably substantially oil free, the term "substantially oil free," is meant that oil substances are preferably not individually added, but may be present due to the natural content of a substance added to the inventive composition. As such, oil may be incidentally present in an amount of less than about 2% by volume, and is preferably incidentally present in an amount of less than about 0.1%, and is most preferably incidentally present in an amount less than about 0.02% and even more so at an amount less than about 0.01%. Additionally, in some instances it may be desirable to add very small quantities of naturally occurring oils or substances, however, the concentration is no more than the incidental amounts discussed above.

Note that penetration inhibiting components, are believed to act as a barrier which seals in toxic irritating by-products of viral growth. They prevent the natural weeping process of the disordered tissue which flows to remove toxins, etc. Accordingly, use of such penetration inhibiting components causes more damage to the disordered tissue despite the temporary advantages achieved though using such substances.

As indicated above, the treatment composition may consist of only the active agent and the carrier. Treatment compositions consisting essentially of the active agent and the carrier do not include penetration inhibiting substances but may include other components added for specific purposes. These components or additives are added to achieve a particular result and do not have a substantial impact on the ability of the treatment composition to penetrate into the disordered tissue or the ability of the treatment composition to be anti-infective. Examples of such components are additives which are conventionally used as preservatives, pH adjusters, substances having anesthetic qualities, vasodilators, analgesics and defoamers. These components or additives are used in concentrations which correspond with amounts conventionally utilized.

Generally, preservatives may be added to the anti-infective composition. Examples of preferred preservatives include parabens, preferably the methyl and propyl parabens. Preferably the preservatives, if present, are supplied to the composition in a range from about 0.0001% to about 0.01% by volume of the treatment composition.

Additives such as those set forth above can be blended with other ingredients to make up the inventive composition including pH adjustors. Such pH adjustors may include organic acids, mineral acids in minute amounts, organic bases or mineral bases also in minute amounts. Preferred organic acids include citric acid, ascorbic acid, sorbic acid, malic acid, ascetic acid, succinic acid, caproic acid, and the like. Other preferred acids include hydrochloric acid, nitric acid, hydroiodic acid, and the like in minute amounts. Preferred bases include methyl and ethylamines such as triethanolamine, and the like. Other preferred bases include, ammonium hydroxide, potassium hydroxide, sodium hydroxide, and the like.

The inventive compositions may include compounds with anesthetic qualities. Depending upon the application site, whether on dermal layers or on mucous membranes, different anesthetics may be preferred. One particularly preferred anesthetic is benzocaine. Benzocaine is especially useful in the areas of open sores such as cold sores, eczema sores, and the like. Of the amides, such compounds as bupivocaine, carbocaine, and ropivocaine may be preferred. Of the esters, such compounds as procaine, cocaine, novocaine tetracaine and benzocaine may be preferred. Other preferred anesthetics include alkaloids such as cocaine, caffeine, nicotine, xylocaine, and the like. Another preferred anesthetic includes a combination of lidocaine and prilocaine. With these two compounds, an eutectic mixture is achieved with a melting point below room temperature. A preferred composition of the lidocaine and prilocaine is about 2.5% each in a 1:1 mixture. Other preferred anesthetics include oil of cloves, tea tree oil (Melaleuca alternifolia, which also acts as a disinfectant) and the like. Other preferred anesthetics include lidocaine hydrochloride, dibucaine, dibucaine hydrochloride, tetracaine hydrochloride, tronothane, dyclonine, dyclonine hydrochloride, pramoxine hydrochloride, diperodon, butamben picrate, cyclomethycaine sulfate, cyclomethycaine hydrochloride, and dimethisoquin hydrochloride. Where an anesthetic is present, it is supplied to make up the composition in a range from about 0.001% to about 0.01% by volume of the treatment composition.

Other preferred components for the inventive composition include vasodilators such as nitroglycerine and the like. Vasodilators are useful for causing penetration of the active agent or agents into the disordered tissue to its base in the skin or mucous membranes an beyond. Care must be taken to balance the effect of localized vasodilation against the systemic toxicity of the inventive composition such that penetration into the disordered tissue is clinically significant, but that the active agent or agents remain substantially local to the disordered tissue for maximum efficacy. Where a vasodilator is supplied to make up the inventive composition, it may be provided in a preferred range from about 0.001% to about 0.05% by volume of the treatment composition.

Other preferred components for the inventive composition include analgesics such as methyl salicylate, aspirin, and other salicylate salts. Other preferred components for their analgesic effects include N,N-dimethyl aspartic acid; N-N-dimethyl glutamic acid, trolamine salicylate, antipyrine, and salicylamide. Where an analgesic is present, it may be supplied to make up the composition in a preferred range from about 0.001% to about 0.01% by volume of the treatment composition.

Most of the active agents disclosed above are considered to be cationic surfactants so it is generally unnecessary to include any surfactants. It is also generally unnecessary to include surfactants as the treatment composition is substantially oil free. Additionally, the active agent can be used with various carriers so the carrier can be modified to achieve optimal solubility as needed. To the extent that a surfactant is included, for example, to assist in tissue wetting properties, the surfactants may be anionic, cationic, or nonionic, and amphoteric. In some circumstances it may be useful to use other surfactants such as: another cationic surfactant, an ampholytic surfactant or a zwitterionic surfactant. U.S. Pat. No. 5,661,170, reference above, may be referred to for a disclosure of suitable surfactants.

Abrasives are generally not necessary as a component of the composition as the applicators are configured for abrasion. Additionally, when irritating an open sore it would be undesirable for abrasives to be deposited into the open sore. Nor is it generally necessary to include abrasives on the applicators, which also risks the abrasives being dislodged from the applicator and into an open sore. However, this does not exclude the use of abrasives as free-floating inert components in a treatment composition nor their surface attachment to or impregnation in an applicator. If used, suitable abrasives may include pumice and the like as well as oxides such as alumina, silica, mica, zirconia, titania (both anatase and rutile), and the like.

In making a mixture of any of the preceding carriers and additives, it is understood that the recitation of compounds as mixtures includes the solution and reaction products thereof. A preferred method for preparing the inventive composition is to dissolve the anti-infective active agent into the carrier, such as to dissolve benzalkonium chloride in isopropyl alcohol. In general, it is only necessary to mix the agent, such as benzalkonium chloride, into the carrier. In some instances, it may be helpful to first lower the pH of the solution into a range preferred to assist the dissolution of selected components. Note that benzalkonium chloride is alkaline. Following dissolution of the selected components that are assisted in their dissolution by a lower pH, the solution may be either warmed or the pH increased, or both, and other components may be added, preceding or following the warming and/or the pH increase.

The use of soap is preferably avoided in the inventive method as it tends to significantly reduce the efficacy of the methodology. However, the inventive method may include a precleaning step that comprises washing the disordered tissue treatment site. The precleaning step may include the use of a pre-moistened, organohalide impregnated towelette, for example a towelette impregnated with benzalkonium chloride such as the PDI® made by Professional Disposables, Inc. of Orangeburg, N.Y. A pre-moistened, benzethonium chloride impregnated towelette is also suitable such as the WET ONES® made by Playtex Products, Inc. of Dover, Del. Note, however, such towelettes contain components which are generally considered undesirable in combination with the present invention. Accordingly, when a precleaning towelette is used, it is preferred that the towelette be moistened with a composition which does not contain any penetration inhibiting components such as lanolin. Additionally, as discussed below, anesthetics may also be impregnated in the pre-moistened towelette. When the towelette is used in the genital area, it has the advantage of preventing the spread of substances contained in the disordered tissue because the towelette is disposed of after a single use.

The cleaning may also be achieved with a towelette that has an abrasive surface as opposed to the relatively smooth towelettes conventionally used for convenient cleaning such as those mentioned above. Cleaning using a towelette that has an abrasive surface may be useful in starting the inventive method where vigorous agitation of the disordered tissue site that is sufficient to significantly awaken the immune response for a synergistic effect. The abrasive surface towelette also has the advantage of removing tissue that is in the process of sloughing off from the disordered tissue site. Such tissue usually provides a hindrance to the inventive method because it prevents application of the anti-infective active agent to living disordered tissue. An abrasive towelette may be selected from existing stock formed from treated natural fibers, synthetic fibers, and untreated natural fibers. One example is a rough paper towel used in the paper towel industry or the like. One of ordinary skill in the art may select a towelette that has the preferred abrasive qualities while maintaining a preferred absorbability in order to convey the anti-infective active agent to the disordered tissue treatment site during precleaning.

In one method of the present invention, a topical anesthetic may be applied to the treatment site and enough time may be allowed to elapse in order to substantially anesthetize the nerve endings for disordered tissue and surrounding tissue at and near the treatment site. After sufficient anesthetization of the treatment site, the inventive method continues by providing the inventive composition that contains the anti-infective agent followed by impregnating an applicator with the composition, or using a pre-impregnated applicator. Finally, the disordered tissue at the treatment site is vigorously agitated with the applicator while contacting the disordered tissue with the composition. According to this alternative inventive method, where a patient may have a low threshold of pain tolerance, the preliminary anesthetization of disordered tissue at and near the treatment site allows for the vigorous irritation of the disordered tissue without the accompanying discomfort.

Another alternative includes the application of a substance in liquid form in order to provide both sterile and cosmetic covering of the disordered tissue after the inventive vigorous agitation treatment. One example of a suitable liquid is NEW-SKIN® Liquid Bandage made by Medtech Laboratories, Inc. of Jackson, Wyo.

Applicators are preferably part of the inventive method and system. As such, applicators may be preconfigured with particular mixtures to treat specific disorders such as cold sores, eczema, and the like. Applicators are well known in the art. Examples thereof include those taught by Booras et al. in U.S. Pat. No. 5,709,866; by Fox in U.S. Pat. No. 5,704,906; by Mythling in U.S. Pat. No. 5,527,534; by Stalcup et al. in U.S. Pat. No. 5,016,651; by Bedford in U.S. Pat. No. 4,887,994; and by Korteweg in U.S. Pat. No. 4,952,204; the disclosures of which are incorporated herein by specific reference. Preferred applicators include prepackaged applicators that have agitation pads impregnated with the inventive composition. An applicator may be provided as a unitary structure such as a sealed container that is frangible and configured for a single use.

Figure 2:
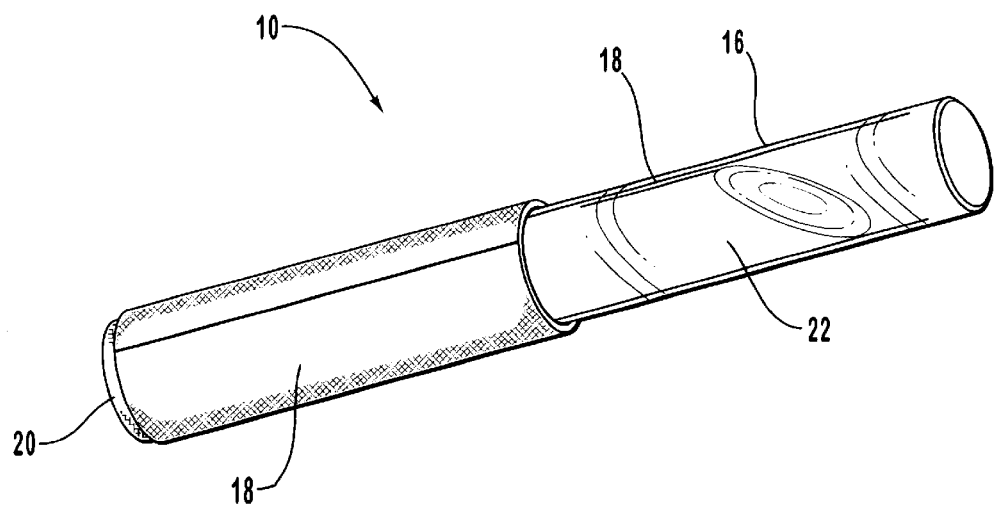
FIG. 2 is a perspective view of the preferred applicator depicted in FIG. 1 as it appears assembled prior to use.

FIG. 1 is an exploded perspective view of a preferred applicator 10. FIG. 2 is a perspective view of the preferred applicator depicted in FIG. 1 as it appears assembled prior to use.

As shown in FIGS. 1–5, applicator 10 includes an absorbent, agitation pad 12, that is abutted against a frangible reservoir 14. Pad 12 is a cluster of fibers or bristles which are able to hold the treatment composition 22 and abrade disordered tissue. Pad 12 is preferably made of synthetic fibers that have a mesh which enables it to hold treatment composition 22 while having sufficient roughness to allow vigorous or continual agitation of the disordered tissue to be penetrated by treatment composition 22. The fibers forming pad 12 are relatively densely positioned and are also relatively rigid. The dense positioning and the rigid nature of the fibers enables applicator 10 to be used to vigorously agitate the disordered tissue. Note that applicator 10 is not used like a brush to merely apply the treatment composition like conventional methodologies which involve coating the afflicted tissue. If the fibers are relatively soft such that they flex significantly when pushed against the disordered tissue then it is necessary to also push relatively hard against the disordered tissue in order to insure that the disordered tissue has been adequately agitated. Accordingly, the fibers are preferably relatively rigid through either proper selection of the fiber material, the length of the fibers and/or the positioning of the fibers. The fibers used in pad 12 are preferably formed from polyester as such polyester fibers provide adequate stiffness at the desired length.

As used in the specification and the appended claims, the term "fibers" includes both synthetic fibers, inorganic fibers, naturally occurring organic fibers and treated organic fibers. Synthetic fibers such polyester fibers are preferred. Another example of synthetic fibers includes polyethylene fibers. Polyethylene fibers having the same length and diameter as polyester fibers are not as preferred as they tend be softer. Of course the abrasiveness of fibers can be increased by increasing the diameter of the fiber; however, it is preferred not to increase the diameter of the fibers as this results in a decrease in surface area for the treatment composition to move downward on the fibers. Examples of inorganic fibers include glass, silica, ceramic, graphite, metal fibers, and mixtures thereof. Glass fibers, such as Cemfill® are available from Pilkington Corp. in England. These fibers are preferably used in the present invention due to their physical qualities. Nevertheless, any equivalent fiber which has the preferred physical qualities such as strength, roughness, ability to hold liquids, and/or proper flexibility is also within the scope of the present invention. The only limiting criteria is that the fibers be able to be configured in manner which enables them to hold the treatment composition and agitate the afflicted tissue without adversely reacting with the chemical constituents of treatment composition 22. Examples of naturally occurring fibers, include cellulosic fibers extracted from abaca, bagasse, hemp, cotton, plant leaves, wood or stems. The wood fibers may be both hard wood or soft wood, such as southern pine. While pad 12 may be made of such organic or naturally occurring fibers, it may be necessary to treat some naturally occurring fibers as discussed hereinbelow.

Frangible reservoir 14 is housed in a container 16 that forms a holder for agitation pad 12. Frangible reservoir 14 is preferably formed from thin glass while container 16 is preferably plastic. A protective sleeve 18 is provided that is designed to keep agitation pad 12 free from contamination until its intended vigorous agitation use on the disordered tissue. A cap 20 is provided to fit into sleeve 18. The treatment composition 22 is held in frangible reservoir 14 until such time as frangible reservoir 14 is to be broken.

Figures 3, 4:
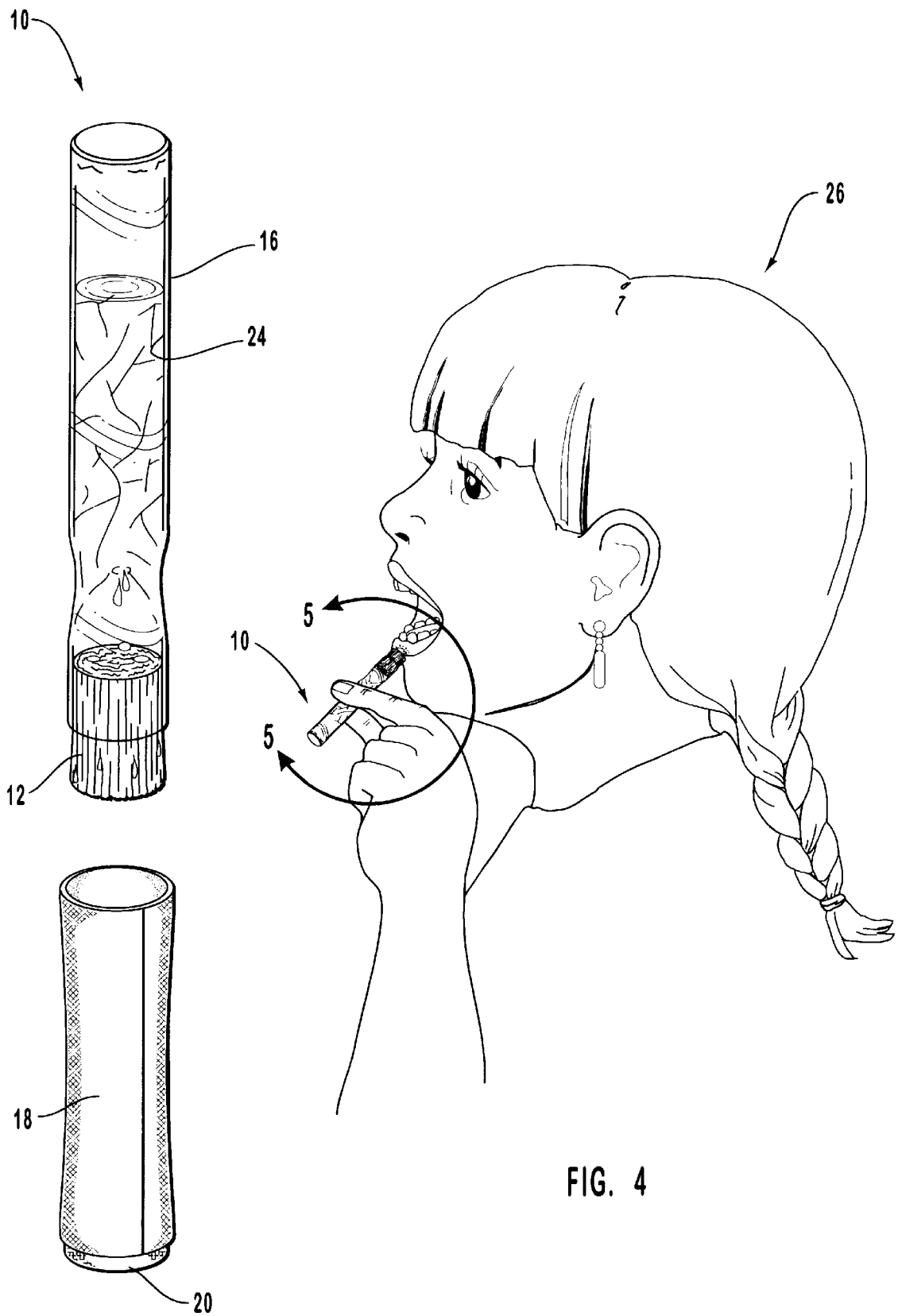
FIG. 3 is a perspective view of the preferred applicator depicted in FIG. 2 after the glass reservoir is crushed and the treatment composition is allowed to permeate the agitation pad.
FIG. 4 is a perspective view of an individual applying the treatment composition according to the present invention.

FIG. 3 is a perspective view of the preferred applicator depicted in FIG. 2 after frangible reservoir 14 is broken. Treatment composition 22 is allowed to permeate agitation pad 12 in preparation for vigorous application to a disordered tissue treatment site. In FIG. 3, sleeve 18 has been removed to expose an impregnated agitation pad 12. After impregnated agitation pad 12 is sufficiently wetted, application to the disordered tissue treatment site may commence.

FIG. 4 is a perspective view of an individual 26 applying treatment composition 22 to a disordered tissue at or near the lip according to the present invention. FIG. 4 illustrates that sufficient pressure is being applied against a non-puckered lip as the lip is pressed against the patient's teeth and/or gums in order to direct focused pressure into the disordered tissue while the active compounds are expressed from impregnated agitation pad 12 and into the disordered tissue. The combined effect of vigorous irritation of the disordered tissue and the administration of treatment composition 22 has the result of surprising therapeutic effects.

Figure 5:
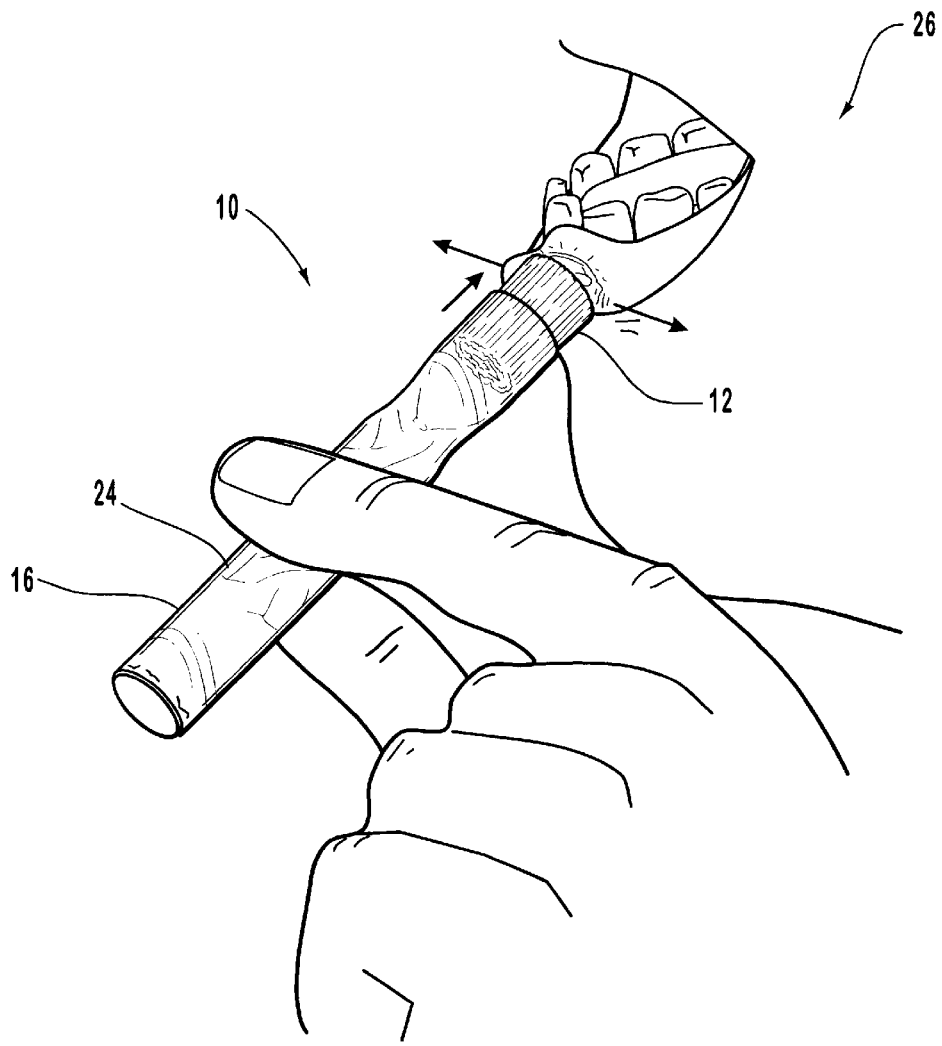
FIG. 5 is a detail taken along the section line 5—5 that depicts a close-up view of the inventive method.
Figure 6:
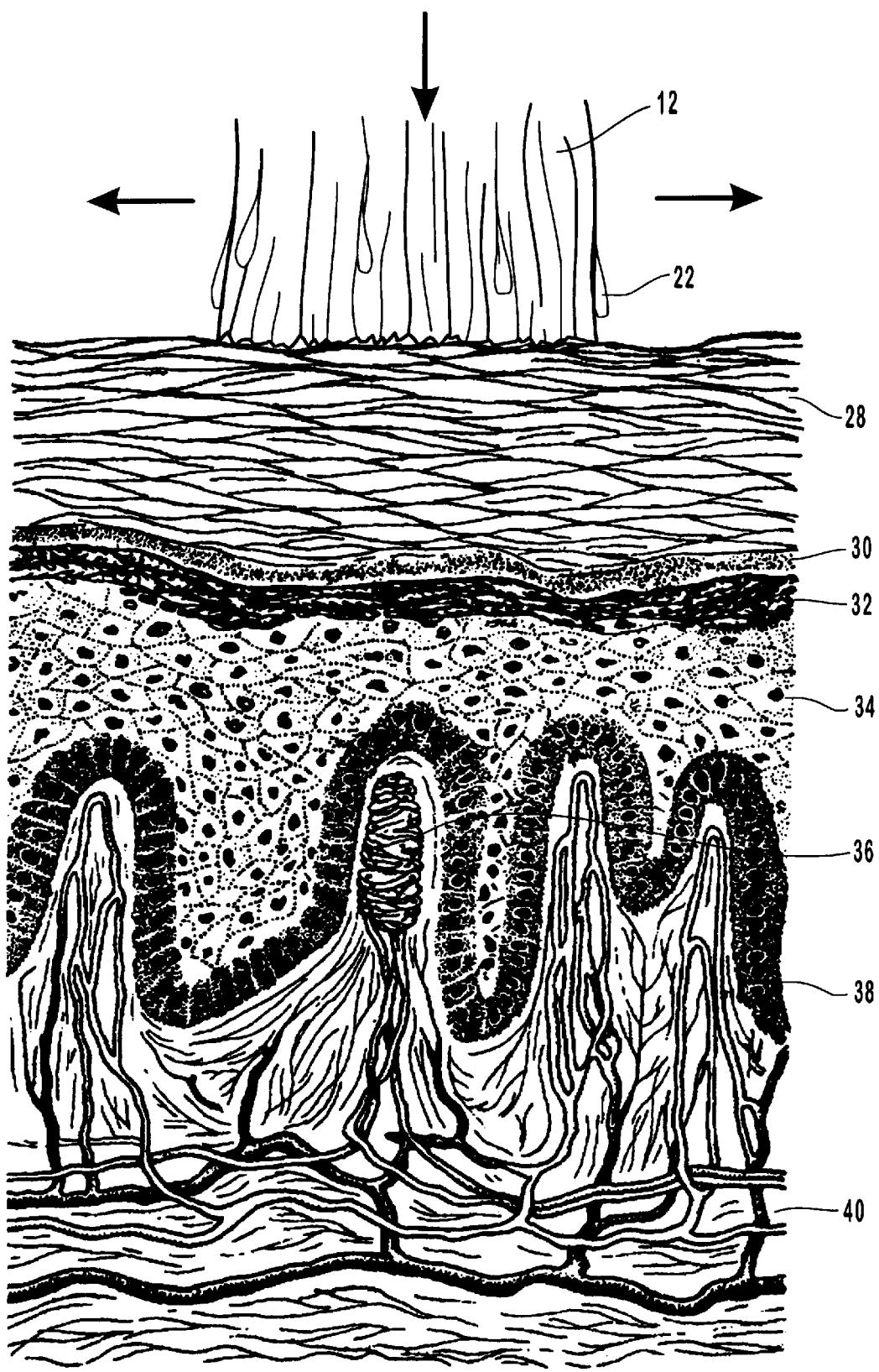
FIG. 6 is a vertical cross-section of the epidermis and the papillae of the dermis.

FIG. 5 is a detail taken along the section line 5–5 that depicts a close-up view of the inventive method. The detail view more clearly illustrates vigorous agitation of the disordered tissue site where impregnated agitation pad 12 is being pressed into the lip in order to be firmly felt at the gums or teeth opposite the disordered tissue. The arrows illustrate directions of agitation movement by way of non-limiting example.

FIG. 6 is a vertical cross-section of the epidermis and the papillae of the dermis. FIG. 6 illustrates the stratum corneum 28 disposed upon the fatty layer or stratum lucidum 30. The stratum lucidum is disposed over the stratum granulosum 32. Below the stratum granulosum 32 is the stratum spinosum 34. Typically, the stratum spinosum 34 has a lipid film disposed around each individual cell. Below the stratum spinosum 34 is the stratum basale 38 that overlies vascularized tissue. Within the vascularized tissue the nervous papilla of the corium 36 is located along with blood vessels and nerves 40. During application of the inventive composition, impregnated agitation pad 12 is vigorously agitated across the stratum corneum 28 in order to allow treatment composition 22 to penetrate therethrough.

The arrows illustrate directions of agitation movement by way of non-limiting example. Note, however, that FIG. 6 does not depict the application of pressure as the objective in FIG. 6 is to show the particular layers involved in their natural positions and once pressure is applied the layers are moved from their natural positions. Although the inventor does not wish to be bound to a single theory, it is postulated that treatment composition 22 may move through the stratum corneum 28 without significant rupture thereof due to the vigorous agitation by impregnated agitation pad 12. Treatment composition 22 can penetrate to the nervous papilla of the corium 36 by the combination of vigorous agitation and the penetrating nature of the carrier. Preferably, vigorous agitation and the combination of the penetrating quality of the carrier are sufficient conditions to cause the anti-infective active agent to penetrate the disordered tissue to a nerve ending such as the nervous papilla of the corium 36. Note the application of pressure further increases the ability of the treatment composition to penetrate as the pressure may flatten or compress the layers and may assist in forcing the treatment composition downward. In any event, under the inventive conditions, penetration to the nerve ending is rapidly accomplished, preferably in several seconds. It is also postulated that treatment composition 22 may reside in reservoir amounts within the stratum spinosum 34 and may diffuse across the stratum basale 38 to the nerve endings.

Figure 7:
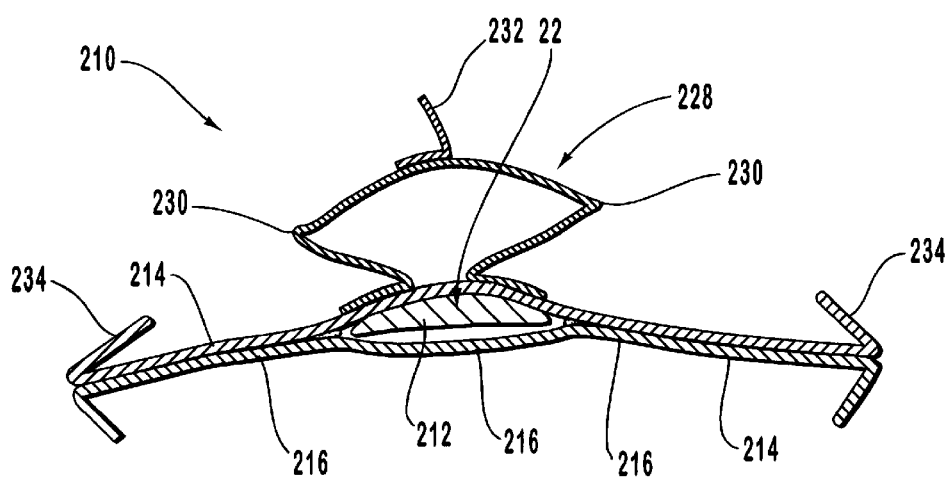
FIG. 7 is an elevational cross section view of an applicator that has a finger loop for vigorous topical irritation of the treatment site.

Another preferred applicator is illustrated in FIG. 7. FIG. 7 is a cross-sectional elevational view of an applicator 210 that may be part of the inventive system and method. Applicator 210 includes an absorbent agitation pad 212 that may be typical of a sterile adhesive bandage. Applicator 210 also includes adhesive wings 214 that may have adhesive typical of a sterile adhesive bandage. A separate strip acts as a container 216 in order to cause treatment composition 22 to remain in agitation pad 212 until container 216 is stripped away from adhesive wings 214 of applicator 210. In addition thereto, a finger loop 228 that may include finger loop folds 230 and a finger loop tab 232 is attached to applicator 210 immediately above agitation pad 212. Finger loop 228 is configured to lie flat against adhesive wings 214 and can be opened by lifting on finger loop tab 232 and hinge open at finger loop folds 230. Applicator 210 may be applied to a treatment site as typical of a sterile adhesive bandage and left in place indefinitely. Additionally, after a selected time period of having applicator 210, particularly agitation pad 212, upon a treatment site, the medical professional or the patient may grab the adhesive wing tabs 234, and gently pull adhesive wings 214 away from the skin. Meanwhile, the medical professional or the patient may insert a finger into finger loop 228, draw adhesive wings 214 also toward finger loop 228 and commence to vigorously agitate the disordered tissue.

Where it is preferable to immediately agitate the cold sore, applicator 210 may be applied at the point of agitation pad 212 onto the disordered tissue and then vigorously agitated against the disordered tissue. Thereafter, applicator 210 may be discarded or adhesive wings 214 may be applied to the patient's skin to allow applicator 210 to remain over the disordered tissue. This alternative may be preferable where bleeding is incidental to the inventive method. As such, applicator 210 doubles as an adhesive sterile bandage.

In summary, applicator 210 may be used only for vigorous irritation of the disordered tissue. It may be used initially for application of the anti-infective active agent without vigorous irritation of the disordered tissue which is then followed by vigorous irritation of the disordered tissue. Vigorous irritation by applicator 210 of the disordered tissue may be alternatively followed by leaving applicator 210 in place like a sterile adhesive bandage.

Figure 8:
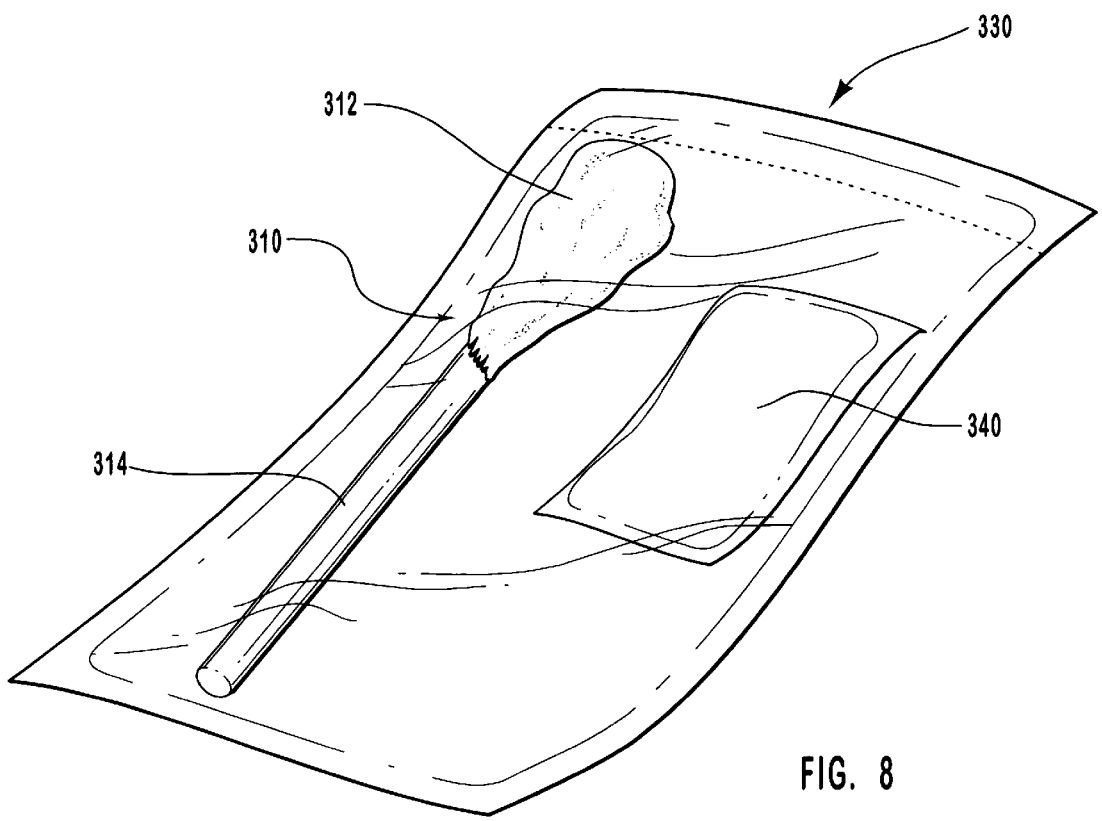
FIG. 8 is an elevational side view of an alternative applicator used in the present invention.

FIG. 8 depicts another applicator at 310 in an elevational side view which may be used in an alternative embodiment of the present invention. The applicator or cotton swab depicted at 310 has a swab agitation pad 312 upon a stem 314. Stem 314 may be formed from any suitable material, however, it is preferably relatively rigid to enable agitation pad 312 to be pushed and/or moved in the desired manner. Pad 312 is preferably used such that the side thereof is pushed against the disordered tissue and not the bulbous tip. The side is used so that sufficient pressure can be applied while using the tip presents certain difficulties. More particularly, when significant pressure is applied, the bulbous tip is likely to dig into the disordered tissue while the surrounding area receives less pressure. Additionally, use of the bulbous tip results in a smaller surface area being contacted which may require agitating different portions sequentially.

It is preferable that the use of swab agitation pad 312 be used under substantially sterile conditions so as to not introduce pathogenic elements into the treatment site of the disordered tissue. The sterile agitation pad of the swab may be dipped into the inventive composition and then used to abrade the skin. More preferably, the swab is held in a bag as shown at 330 which also holds a burst pouch as shown at 340. Burst pouch 340 holds the treatment composition and is sized and/or positioned within the bag such that upon bursting it saturates the cotton swab. An example of a bag holding a swab and a burst pouch designed to be frangible is disclosed in U.S. Pat. No. 5,709,866 to Booras, which was previously referenced.

An applicator and a burst pouch may also be held in separate compartments of a bag such as bag 330 with a perforated divider. Similarly, an applicator and a frangible reservoir such as frangible reservoir 14 may be held in separate compartments. The advantage of this arrangement is that the burst pouch or frangible reservoir can be ruptured to enable the treatment composition to flow into contact with applicator. When a frangible glass reservoir is used, the perforation prevents glass from contacting the applicator.

Fibers such as cotton are not preferred for holding the treatment composition while agitating the disordered tissue as extended exposure to cotton appears to reduce the efficacy of the methodology. Accordingly, when swab agitation pad 312 is formed from cotton, it is preferred that the pad not be stored in contact with the treatment composition. The use of a container such as burst pouch 340 when swab agitation pad 312 is formed from cotton achieves this objective. Applicators such as a swab may be stored in the same container as the treatment composition when swab agitation pad 312 is formed from synthetic materials, naturally occurring fibers which do not reduce the efficacy of the methodology, or fibers such as cotton which have been appropriately treated. Examples of suitable fibers include those discussed above in reference to applicator 10. Examples of a single bag or container for holding a swab are disclosed in U.S. Pat. No. 5,704,906 to Fox and U.S. Pat. No. 4,952,204 to Korteweg which were both previously referenced. Note that bag 330 and burst pouch 340 may be formed from any suitable materials and in any suitable manner.

Due to the relatively smooth texture of the cotton portion of most conventional swabs, when such swabs are used it is typically necessary to apply much more pressure than when an applicator such as applicator 10 or 210 is utilized. Additionally, an applicator such as applicator 10 is further preferred as applicator 10 enables the treatment composition to be continuously delivered without requiring rewetting as a swab may.

The swab agitation pad may be replaced with a sponge to agitate disordered tissue. An example of a foam pad or sponge mounted on a stick such as stem 314 is disclosed in U.S. Pat. No. 4,887,994 to Bedford which was previously incorporated. Reference is made in U.S. Pat. No. 4,887,994 at column 2, lines 44–46 to coarse foam pads, such coarse foam pads are preferred for use as an agitation pad in accordance with the present invention. Coarse foam pads enable the disordered tissue to be more easily agitated through combined rubbing and application of an appropriate amount of pressure than softer foam pads. The coarse foam pad may also be utilized with a stick or stem.

Applicator 310 may also be replaced by an abrasive towelette as discussed above. The towelette fiber may be formed from fibers such as those discussed above in reference to applicator 10. These abrasive towelettes are distinguished from conventional towelettes used for cleaning hands, etc. Conventional towelettes are typically are too thin to hold adequate amounts of moisture while an abrasive towelette preferably has sufficient thickness to hold adequate amounts of the treatment composition. Accordingly, pushing such conventional smooth towelettes in a very hard manner against disordered tissue in order to agitate the disordered tissue does not deliver adequate treatment composition. Additionally, while such a conventional smooth towelette may be pulled over one's finger to rub against the disordered tissue it has inadequate roughness to agitate the disordered tissue. Further, such a conventional smooth towelette may be scrunched in order to better hold the towelette while rubbing the disordered tissue and to concentration the moisture held in the towelette, however this would result in folds, some of which may dig into the disordered tissue if it is an open sore. In any event, folds resulting from drawing the towelette together prevent the towelette from being used to uniformly agitate disordered tissue.

Like the swab shown at 310, the other embodiments discussed above may be stored and used in a similar manner. More particularly, the coarse foam pad on a stick, the coarse foam pad alone, or the towelette may be held in a bag or other sterile container such as is shown at 330 along with a burst pouch as shown at 340. Additionally, these applicators may be held in a bag such as bag 330 without a burst pouch 340 in a dry sterile condition for dipping into a separate reservoir of the treatment composition or the treatment composition may be held in the bag along with the applicator.

Figure 9:
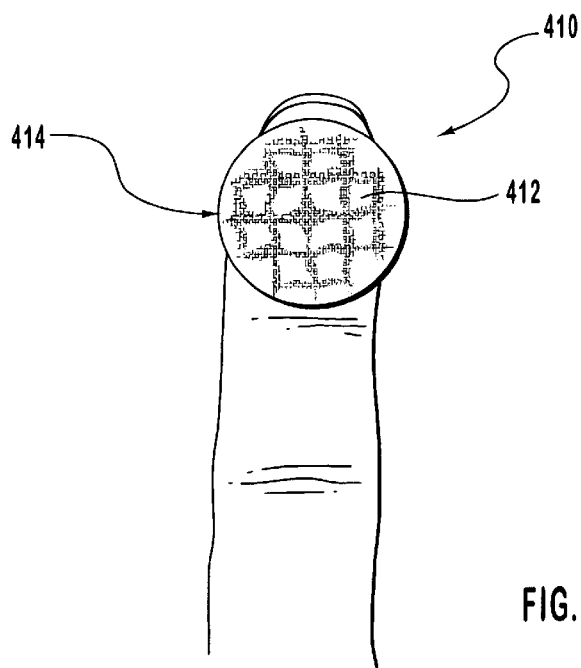
FIG. 9 is an elevational side view of an alternative applicator that is fixed to a digit for vigorous topical irritation of the treatment site.

FIG. 9 is an elevational perspective view of an alternative applicator that includes a fingertip applicator 410. Fingertip applicator 410 includes an absorbent, agitation pad 412 held on an adhesive surface 414 that the individual being treated or the medical professional applies to the fingertip. Agitation pad 412 may include an absorbent material for retaining the treatment composition and it may alternatively contain fixed abrasive elements to assist in the vigorous irritating of the disordered tissue at the treatment site.

Figure 10:
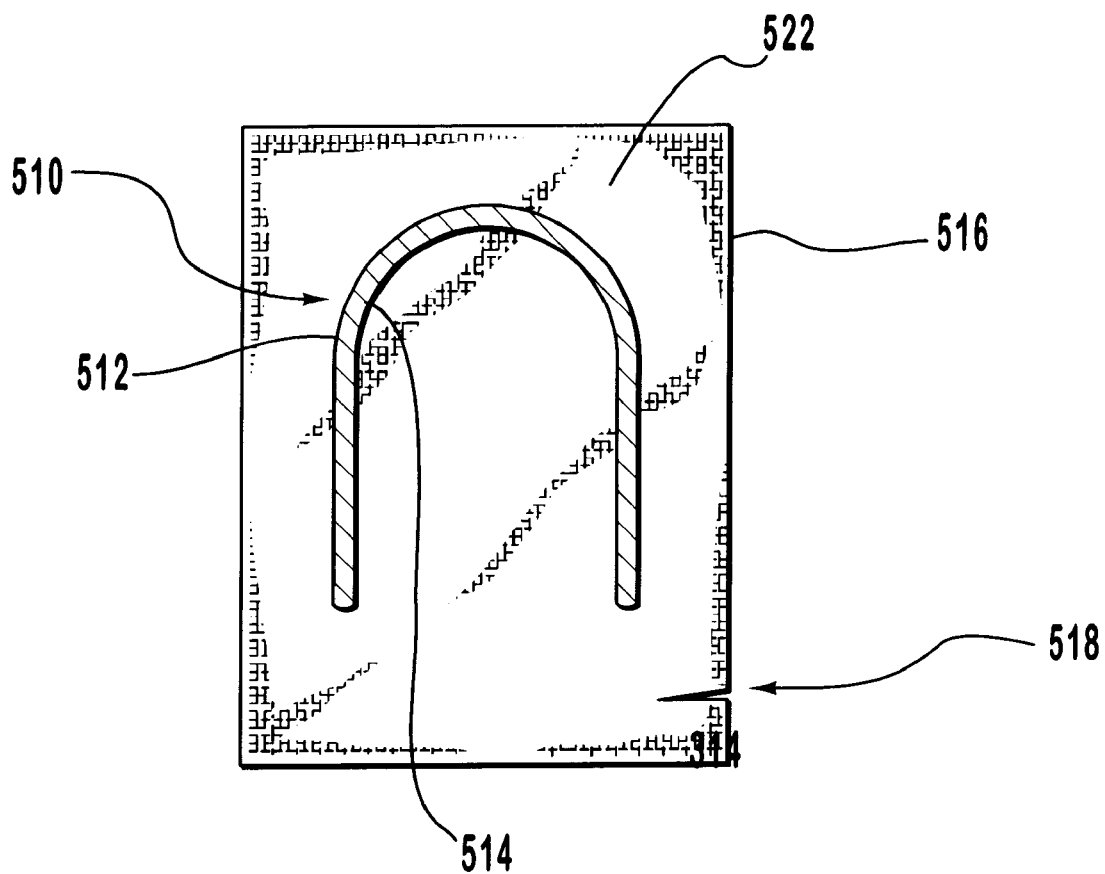
FIG. 10 is a cross-sectional plan view of an alternative applicator that is placed over a digit and that is contained in a pre-wetted state before use.

FIG. 10 is an elevational cross-section view of an alternative applicator that includes a finger- or digit-container applicator 510. Digit-container applicator 510 includes an absorbent, agitation pad 512 with a first side 512 that acts as the agitation pad 516, and a second side 514 that acts at the support 514. The user may rupture the container 516 such as by tearing a slit 518 and inserting a finger into applicator 510 against second side 514. Container 516 is a bag like that shown at 330 and may be referred to as what is commonly called a pillow pouch or package. Container 516 may also contain a burst pouch such as burst pouch 340. Applicator 510 is, however, preferably pre-moistened by the presence of treatment composition 522 within container 516. Applicator may also be held in a container 516 in a dry sterile condition for dipping into a separate reservoir of the treatment composition.

First side 512 is made of an absorbent and abrasive material that is substantially uniform in relation to the size of a disordered tissue site. First side 512 preferably has the approximate roughness of a conventional gauze bandage or terry cloth. However, first side 512 and/or second side 512 are not necessarily formed from cotton. In fact, as discussed above, cotton is preferably not used unless it has been appropriately treated not to absorb the treatment composition, particularly the benzalkonium chloride.

Preferably, first side 512 is seamless and devoid of fabric folds etc. Additionally, where second side 514 is used to interface with a finger, it is a support for first side 512 as the agitation pad and delivery portion of applicator 510. As a structural explanation of applicator 510, if applicator were to be turned inside-out, first side 512 would be under compressive stress and second side would be under tensile stress.

The above embodiments comprise examples of an inventive method and system of treating disordered tissue. It is preferred not to dip a bare finger into a container of the treatment composition because oils or other materials contained on the finger may be of sufficient amount to cause the treatment composition to be rendered ineffective. Additionally, back contamination of composition in the container may occur. The agitation pads 12, 212, 312 412 as well as first side 512 are examples of a delivery and agitation means for delivering the treatment composition and for agitating the disordered tissue of the patient. Note that other examples include an abrasive towelette and a coarse foam pad. As discussed above, a conventional smooth towelette is not an example of a delivery and agitation means.

The container 16 of applicator 10, the finger loop 228 of applicator 210, the stem 314 of applicator 310 or similar applicators, the adhesive surface 414 and the second side 514 of applicator 510 are examples of a means for supporting the delivery means.

A coarse foam pad, pad 212, pad 412 and first side 512 are all examples of delivery and agitation means capable of conforming to the surface features of the disordered tissue as the corresponding supporting means also conforms to the surface features. Stated otherwise, the applicator is flexible such that both the delivery and agitation means as well as the supporting means flex in conformance with the surface anatomy of the disordered tissue. First side 512 is particularly useful for adapting to the surface anatomy of the disordered tissue.

The frangible reservoir 14, container 216, and container 516 are examples of a reservoir means for containing the composition. Additionally, a bottle or the like that contains treatment composition 22 for use with applicator 310 is another example of a reservoir means for containing the composition. Note that reservoir 14, container 216 and container 516, however, are configured to be in fluid communication with the delivery and agitation means. Frangible reservoir 14 and burst pouch 340 are configured to be in fluid communication with the delivery and agitation means once ruptured. Frangible reservoir 14 is further configured to continually deliver the treatment composition to the delivery and agitation means while the delivery and agitation means is agitating the disordered tissue until all of the treatment composition has been delivered. Note that one of the primary distinctions between frangible reservoir 14 and burst pouch 340 is that the frangible reservoir 14 is located within the container 16.

Container 516 and bag 330 are examples of container means for holding the applicator. This configuration, as discussed above, enables the applicator to be held in a dry sterile condition for dipping into a separate reservoir of the treatment composition. As also indicated above, container 516 and bag 330 can also bold the treatment composition along with the applicator such that the applicator is pre-moistened. Accordingly, container 516 and bag 330 are also examples of container means for holding the applicator and the treatment composition. As further indicated above, container 516 and bag 330 can also hold the treatment composition in a pouch along with the applicator. On this basis, container 516 and bag 330 are also examples of container means for holding the applicator and a reservoir means.

The inventive method of treating disordered tissue and the like includes impregnating an applicator with the inventive anti-infective composition and contacting the treatment site with the applicator. Vigorous agitation of the disordered tissue is particularly useful as the induced physical trauma causes the awakening of the body's immune response local to the irritation. As such, the immune response and the penetration of the inventive composition into the disordered tissue has the concerted effect of a rapid decline of the infection.

Chemotaxis, the migration of phagocytes such as granular leucocytes and human leucocyte associated (HLA) antigens to an area of a tissue disorder, is enhanced and assisted in the present invention by the vigorous agitation of the disordered tissue with the anti-infective active agent or agents. The combination of the anti-infective active agent, preferably benzalkonium chloride, with the chemotaxis phenomenon caused by the vigorous agitation of the disordered tissue, has the surprising effect of a rapid decline of the infectant such as a virus or a microbe in the disordered tissue. Note that one type of granular leucocyte, the neutrophil, has the ability to activate defenses which are amino acids that exhibit a broad range of antibiotic activity against bacteria, fungi, and viruses. Consequently the synergistic effect of vigorous agitation is rapid delivery and the awakening of the immune response. The neutrophil, if activated is therefore useful to treat disordered tissue according to the present invention where bacteria, fungi, or virus infections occur. Further, agitation causes fluids to concentrate in the area of the disordered tissue which further enables the active agent to move as needed in order to penetrate effectively.

Other immune responses may occur with the vigorous agitation of the disordered tissue site by the inventive method, and the inventors do not wish to be bound to any single theory that may explain the surprising efficacy of the inventive method and system.

EXAMPLES OF THE PREFERRED EMBODIMENTS

The following examples are provided as illustrative of the inventive method and system. These examples are not intended to be limiting of the invention. The examples all produce clinically discernable improvement of disordered tissue. By "clinically discernable improvement of disordered tissue," it is understood that various testing methods may be used to quantify improvement of disordered tissue. One example of clinically discernable improvement of disordered tissue include arresting the normal progression of a tissue disorder such as a cold sore. Another example of clinically discernable improvement of disordered tissue is healing of a tissue disorder at a faster rate than was observed before in a recurrent disorder such as a cold sore. Another example of clinically discernable improvement of disordered tissue is an arrest of pain usually associated with the progression of a tissue disorder such as a cold sore. Another example of clinically discernable improvement of disordered tissue is the permanent deactivation of a recurrent tissue disorder site after the inventive method is applied to a disordered tissue site.

The clinical examples provide hereinbelow were performed with a treatment composition which included benzalkonium chloride. The carrier was 30% by volume water and 70% isopropyl alcohol by volume of the carrier. The treatment composition was prepared with about one part benzalkonium chloride to about 750 parts carrier. More particularly, 5 drops of benzalkonium chloride having a concentration of about 17% in isopropyl alcohol were added for each ounce of the carrier. The result was a treatment composition containing about 0.0133% benzalkonium chloride by volume of the treatment composition. Although additives and other constituents may be combined with the mixture as set forth above these particular test treatment compositions did not include any additives.

As discussed above, the methodology in the examples includes vigorously applying the composition to the disordered tissue and removing the superficial lipids by the carrier. The carrier also is useful for the penetration of the disordered cells at the tissue disorder site. Either following or simultaneously with the penetration of disordered cells with the composition at the tissue disorder site, vigorous agitation of the tissue with the composition is carried out under conditions to increase the flow of intercellular fluid to the tissue at the tissue disorder site. This enables the active agent greater ease of transportation at the site to better penetrate.

CLINICAL EXAMPLES

Clinical Example 1

A male was diagnosed with several vesicles beginning to coalesce on the lip. Treatment was initiated immediately.

After about 1 day, it was observed that the vesicles had not coalesced further and that progression of the cold sore through its normal stages was arrested. After about two days, scab tissue was observed to be sloughing off. After about seven days, no sign was left of the disordered tissue. The patient observed that for previous eruptions the complete healing of this cold sore at this site took from about two to three weeks.

Clinical Example 2

A male was diagnosed with a cold sore erupting below the corner of the mouth. The usual tingling and tightening sensation that occurs with a cold sore onset was observed by the patient. The inventive composition and method was applied to the patient according to the inventive method. Immediately upon application, the usual tingling and tightening sensation was not noticed. After about two days, no visible sign of a cold sore was observable.

Clinical Example 3

A male with a history of cold sores ranging in a size from about 1.5 cm to about 2.5 cm in diameter was treated immediately upon sensing the tingling and tightening of an oncoming cold sore. A numbing sensation was immediately noticed and the pain was gone. After about 3 days, the cold sore had begun to heal.

Clinical Example 4

A female was diagnosed with pustules and vistules upon the lower lip. The inventive composition was applied to the patient according to the inventive method, and pain was gone as soon as the application of the inventive composition was done. Instead of the normal weeping and scabbing the patient was used to, the cold sore healed without weeping or scabbing, and pain was minimal in comparison to previous experiences.

Clinical Example 5

A female had a disordered tissue eruption upon a digit with about 7 vistules in the pre-eruption stage. The blistering typical of this type of tissue disorder began to fade immediately after application of the inventive composition. A small amount of scaling was observed after about 2 weeks. The patient observed that the normal course of an eruption and healing at this cold sore site was shortened by the inventive composition and method.

Clinical Example 6

A female was diagnosed with a cold sore taking up about one-half of the area of the lower lip. The cold sore had multiple lesions. The inventive composition was vigorously applied to the cold sore. Pain was immediately relieved and weeping was immediately arrested from the cold sore.

Clinical Example 7

A female observed tingling and tightening upon the inside of her lip in the evening and observed one small pustule and three to four vistules at the time of treatment the next morning. The inventive composition was applied by vigorous rubbing with a cotton swab. A second treatment was carried out that evening, and a third treatment was carried out the following morning. The pain was observed to be relieved fairly quickly upon the first treatment. The patient observed that the inventive composition and method worked at least as well as her usual Zovirax® prescription, manufactured by Glaxo Wellcome Inc. of Research Triangle Park, N.C. The following advantages of the inventive composition and method were observed in comparison. One advantage was that fewer applications were required. Additionally, no unpleasant tasting ointment remains upon the lip during the treatment time.

Clinical Example 8

A female with a cold sore history including at least one eruption per month was diagnosed with some yellow scabbing present upon a cold sore site. After vigorous irritation of the disordered tissue with the inventive composition, the patient observed that pain was completely gone after about seven hours.

Clinical Example 9

A male was diagnosed with a cold sore upon the lower lip. The inventive composition was applied by rubbing. The cold sore was observed to be healed after two days.

Clinical Example 10

A male was diagnosed with a number of cold sores at the corner of the mouth and above the lip. Prior to vesicular eruption, the usual pain that precedes the eruption of a cold sore was observed about 24 hours previously. The inventive composition was applied by rubbing. Growth of the disordered tissue was immediately arrested and the tissue appeared to have cleared in three days following the treatment.

Clinical Example 11

A female diagnosed with a cold sore upon the chin about halfway between the base of the chin and the lower lip. The inventive composition was applied with rubbing. The cold sore was observed to have healed within about two days.

Clinical Example 12

A six year old female was diagnosed with an open cold sore upon the lower lip. The inventive composition was applied by vigorous rubbing. The cold sore was barely observable in about three days.

Clinical Example 13

A male was diagnosed with a cold sore upon the lower lip. The inventive composition was applied by vigorous rubbing. The progression of the cold sore was arrested and pain was stopped within a few minutes.

Clinical Example 14

A female was diagnosed with a cold sore at the corner of the mouth that would crack when the mouth was opened. The inventive composition was applied by vigorous rubbing. Within about two days, the cold sore was observed to be completely healed. The patient observed that cold sores in the corner of the mouth of this type usually took at least 7 to 10 days to heal.

Clinical Example 15

A three-year old male was diagnosed with a cold sore upon the lip. The inventive composition was applied by vigorous rubbing. It was observed that progression of the cold sore was immediately arrested and that the cold sore did not form at that site again. The patient had about six sites that erupted upon the lips frequently, and no treated site re-erupted after treatment.

Clinical Example 16

A four-year old male with a history of about 25 oral cold sores was treated by vigorous agitation of the disordered tissue upon a re-eruption of each untreated cold sore. Pain was observed to cease immediately upon treatment. Additionally, the cold sore did not erupt again at any of the specific treatment sites even after a year.

Clinical Example 17

A male was diagnosed with a cold sore below the corner of the lower lip. The inventive composition was applied by vigorous rubbing. Immediately upon application, the tingling sensation that accompanied the cold sore was gone. The next morning the cold sore had closed and was scabbed and healing. Within two days of the application, the cold sore was completely healed. The patient observed that normal healing time, before the inventive treatment, took about two weeks.

Clinical Example 19

A male was diagnosed with a cold sore in the vistial stage upon the lower lip. The inventive composition was applied by vigorous rubbing. The cold sore was observed not to progress beyond the vistial stage. Healing occurred without pain and throbbing. The cold sore was totally healed within seven days.

Clinical Example 20

A female was diagnosed with two cold sores upon the lower lip. The inventive composition was applied by vigorous rubbing between about 30 and about 60 seconds. No pain was felt after the vigorous rubbing. Two days later, one of the cold sores was gone and the other one had a slight scab that was also gone after three more days.

Clinical Example 21

A female was diagnosed with a cold sore that was about 2 cm across and generally round in shape, below one corner of the lower lip. The inventive composition was applied by vigorous rubbing. The patient described the cold sore to be burning and weeping. Within about one minute of treatment, the burning had stopped. Within hours, the weeping stopped and a normal or non-cold sore scab appeared. Within days, the cold sore was gone and healed. No re-occurrence of the cold sore was observed.

Clinical Example 22

A male was diagnosed with an extremely swollen, red and weeping cold sore above one eye. The inventive composition was applied by vigorous rubbing to the cold sore. The swelling and redness were reduced within minutes of the treatment. By the next morning, the cold sore appeared to be a normal or non-cold sore scab. Complete healing was observed after about four days.

Comparative Clinical Example 1

A female was diagnosed with a cold sore above the upper corner of the upper lip. The inventive composition was applied but only slight rubbing occurred. Soap was used on the cold sore treatment site that evening. Although the cold sore formed a scab after about two days, a new cold sore erupted at that time above the existing scab and spread itself into the scab.

Clinical Example 21

A female was diagnosed with a canker or ulcer. The inventive composition was applied by vigorous rubbing until blood was seen on the cotton swab. The patient observed that the canker was gone after only about two or three days. When the patient was reexamined one week after the treatment, there was no sign of the canker.

Clinical Example 22

A male was diagnosed with shingles in two eruptions; one upon the face over the cheekbone and the other upon the back of the neck. The inventive composition was applied by vigorous rubbing to the eruption upon the face. Immediate reduction in discomfort was observed. The redness also immediately began to fade. The patient used shaving soap the same day following treatment and observed that the eruption on the face was returning. A second treatment was repeated in the same manner and progress was again arrested. The treatment site was not contacted the second time with any soap. The eruption on the face healed completely while the eruption on the back of the neck remained even after about four weeks. Treatment was carried out on the eruption on the back of the neck and the eruption was healed in a few days.

Clinical Example 23

A female was diagnosed with a rash of shingles across the midsection above and at the naval. The inventive composition was applied by extensive and vigorous rubbing for about 20 minutes. The progression of the rash was immediately arrested and no new outbreaks were observed. The rash had been growing from small spots into large sores.

Clinical Example 24

A number of patients with primary eruption cases were treated by the inventive method. It was observed that in each patient, there was no reoccurrence of cold sores, as is typical with untreated primary occurrences.

Clinical Example 25

An individual was diagnosed with what appeared to be a spider bite upon the lower calf area of the leg from a Brown Recluse. A "bullseye" discoloration was observed at the bite location with a brown-red middle region and a red circumferential region. The entire area affected by the venom appeared to be about eight to about nine centimeters in diameter. The inventive composition was applied by vigorous rubbing. After an overnight wait following treatment, the discoloration was not observable. A scab that formed at the center of the bite, fell off after about three days.

Other ways to evaluate the progression of the cold sore healing process include measuring the size of the cold sore and also the degree of inflammation thereof. One such method of evaluation is colorimetry of inflamed tissue that creates a color scale that has apparently healthy tissue of the patient as the baseline, and ranks the inflamed color with some external standard or that nominalizes the inflamed tissue such as being at a nominal red scale of 10. A "nominal red scale" is defined as assigning the tissue color a nominal 10; a nominal zero being undisordered tissue of the same type for the specific patient. Clinically discernable improvement of inflamed tissue is defined as reducing in the nominal red scale within about 24 hours by as much as about two or more on the nominal red scale of 10. With a disordered tissue having substantially no clinically discernable improvement of disordered tissue, a red scale decrease of below about one or less within 24 hours is observed.

Another method is the assay of eosinophils and other immune response substances in the inflamed area before and after the inventive method of treatment. Where the presence of eosinophils and the like increases by more than about 10% within about one hour of the inventive method of treatment, as opposed to less than about 10% increase in eosinophils and the like with a control cold sore, a clinically discernable improvement has occurred.

The following are hypothetical examples. These hypothetical examples include treatment compositions utilizing organochlorides other than benzalkonium chloride. More particularly, these organochlorides include: benzethonium chloride, methyl benzethonium chloride, cetyl pyridinium chloride, chloroxylenol, hexachlorophene, triclosan, chlorhexidine. Their chemical structures are also provided to show that a variety of organochlorides which differ structurally may be utilized. These organochlorides are also used at various concentrations. Additionally, different carriers are utilized.

EXAMPLE 1

In a first example, disordered tissue that has a redness of 10 of a nominal red scale is subjected to the inventive method by impregnating an applicator with about 0.02% benzalkonium chloride in isopropyl alcohol composition. The impregnated applicator is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined and is found to have a decreased nominal red scale to about 6 after about 24 hours and an increased eosinophil assay of about 40% before about one hour.

COMPARATIVE EXAMPLE 1

In a first comparative example, an applicator with about 0.02% benzalkonium chloride in isopropyl alcohol is gently applied to a disordered tissue by dabbing such that substantially no pressure is applied sufficient to depress the tissue against hard tissue that lies underneath. The impregnated applicator is applied to a labial disordered tissue for a time period of about 30 seconds. During the application time period, about 0.1 ml of the inventive composition is absorbed into the patient's disordered tissue. The patient's disordered tissue is estimated to have an area of about 0.5 cm$^2$. The patient's disordered tissue is then examined and is found to have a decreased nominal red scale from 10 to about 9 after about 24 hours and an increased eosinophil assay of about 5% before about one hour.

COMPARATIVE EXAMPLE 2

In another example comparative to the first example, a disordered tissue is treated substantially the same as in the first example with the exception that only isopropyl alcohol is impregnated in the applicator. The patient's disordered tissue is examined after the treatment and is found to have an unchanged nominal red scale score of 10 and a negligibly increased eosinophil assay. However, note that some reduction of redness occurs when just alcohol is used, especially when the disordered tissue is an open sore, as the alcohol tends to wash away toxic material. The redness returns as does the pain as toxins continue to build up since the source of the infection has not been eliminated. Note also that in the United States, alcohol cannot be listed as an active agent in the treatment of cold sores caused by herpes.

EXAMPLE 2

In a second example, all conditions are the same as in the first example with the following variations. An embodiment of the inventive composition is applied to a typical sterile bandage and left over the patient's disordered tissue for about one hour. The sterile bandage may double as part of the applicator. The composition contains, in addition to about 0.02% benzalkonium chloride in isopropyl alcohol, about 5% of a composition of lidocaine and prilocaine in about a 1:1 mixture. After the one hour time period, the patient's skin is substantially numbed, and the applicator is vigorously rubbed into the disordered tissue for about 30 seconds. The patient experiences significantly less pain than that experienced in the first example. The patient's disordered tissue is then examined and is found to have a decreased nominal red scale to about 3 from a beginning of eight after about 24 hours and an increased eosinophil assay of about 50% before about one hour.

COMPARATIVE EXAMPLE 3

In a second comparative example, all conditions are the same as in the second example except that no agitation of the disordered tissue occurs. The patient again experiences a numbing sensation after contact of the inventive composition with the cold sore, but is found to have a decreased nominal red scale to about nine and an increased eosinophil assay of about 10% before one hour.

COMPARATIVE EXAMPLE 4

In another example comparative to the second example, the applicator is impregnated with the lidocaine: prilocaine mixture in isopropyl alcohol but no benzalkonium chloride or any other active agent is included. The patient's disordered tissue is then examined and is found to have a nominal red scale of about nine and a negligibly increased eosinophil assay before one hour.

EXAMPLE 3

In a third example, a patient with pink eye is administered the inventive composition containing about 0.01% benzalkonium chloride in a carrier that is substantially nonirritating to the sclera and supporting eye tissue. The patient, with washed and disinfected hands, then rubs the closed eyelid with the hand or fingers for about 30 seconds. The patient's eye is then examined and is found to have a decreased nominal red scale to about 1 after about 24 hours.

COMPARATIVE EXAMPLE 5

In a third comparative example, a patient is treated exactly as in the third example except that no rubbing through the closed eyelid is carried out. The patient's eye is then examined and is found to have a decreased nominal red scale only to about 7 after about 24 hours.

COMPARATIVE EXAMPLE 6

In another comparative example to the third example, the patient with pink eye is administered with a carrier but with no active agent therein. The patient's eye is then examined and is found to have a decreased nominal red scale to about 8 after about 24 hours.

EXAMPLE 4

In this example, a treatment composition is formed with benzethonium chloride as the active agent. Hereinbelow is the chemical structure of benzethonium chloride:

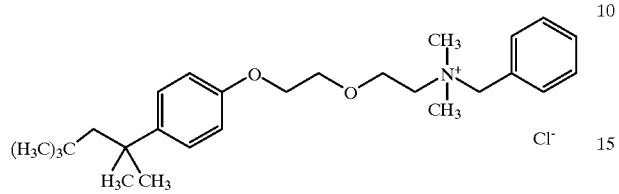

The treatment composition is applied to disordered tissue like that in Example 1 which has a redness of 10 or a nominal red scale. The disordered tissue was on the patient's back. Note that when the treatment compostion is applied to thicker sections of skin such as occur on the back it is more difficult to penetrate than on thinner sections such as the lip or cheek. Accordingly when treating such thick skin portions, it is necessary to increase the active agent concentration, rub and/or press harder, or agitate more frequently. The treatment composition includes about 0.01% benzethonium chloride in isopropyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 5

In this example, a treatment composition is formed with methyl benzethonium chloride as the active agent. Hereinbelow is the chemical structure of methyl benzethonium chloride:

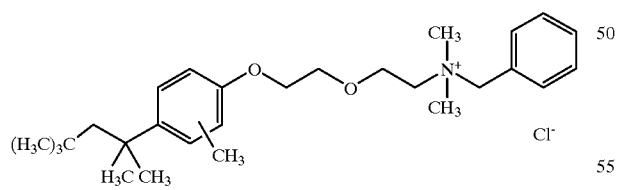

The treatment composition is applied to disordered tissue like that in Example 1 which has a redness of 10 or a nominal red scale. The treatment composition includes about 0.02% methyl benzethonium chloride in a carrier comprising about 70% isopropyl alcohol by volume of the carrier and about 30% water. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 6

In this example, a treatment composition is formed with cetyl pyridinium chloride as the active agent. Hereinbelow is the chemical structure of cetyl pyridinium chloride.

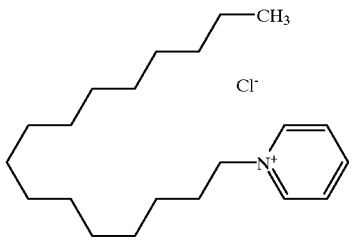

The treatment composition is applied to disordered tissue like that in Example 1 on a patient's arm which has a redness of 10 or a nominal red scale. The treatment composition includes about 2.0% cetyl pyridinium chloride in a carrier comprising about 60% isopropyl alcohol by volume of the carrier, about 30% water and 10% acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 7

In this example, a treatment composition is formed with chloroxylenol as the active agent. Hereinbelow is the chemical structure of chloroxylenol.

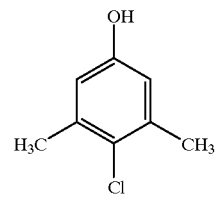

The treatment composition is applied to disordered tissue like that in Example 1 which has a redness of 10 or a nominal red scale. The treatment composition includes about 0.5% chloroxylenol in acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 $cm^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 8

In this example, a treatment composition is formed with hexachlorophene as the active agent. Hereinbelow is the chemical structure of hexachlorophene.

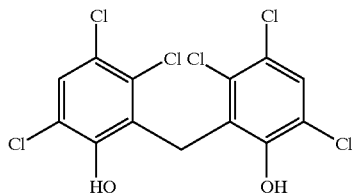

The treatment composition is applied to disordered tissue like that in Example 1 which has a redness of 10 or a nominal red scale. The treatment composition includes about 0.04% hexachlorophene in a carrier comprising about 80% isopropyl alcohol by volume of the carrier, about 15% water and 5% cetyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 9

In this example, a treatment composition is formed with triclosan as the active agent. Hereinbelow is the chemical structure of triclosan.

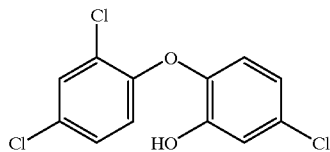

The treatment composition is applied to disordered tissue like that in Example 1 which has a redness of 10 or a nominal red scale. The treatment composition includes about 0.01% triclosan in a carrier comprising about 60% methyl alcohol by volume of the carrier, about 30% water and 10% acetone. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

EXAMPLE 10

In this example, a treatment composition is formed with chlorhexidine as the active agent. Hereinbelow is the chemical structure of chlorhexidine.

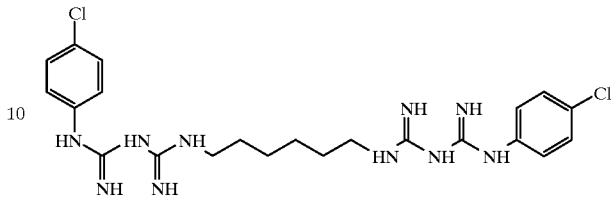

The treatment composition is applied to disordered tissue like that in Example 1 which has a redness of 10 or a nominal red scale. The treatment composition includes about 0.03% chlorhexidine in methyl alcohol. An applicator impregnated with the treatment composition is then vigorously applied to a labial disordered tissue for a time period of about 30 seconds. During the application time period, about 0.2 ml of the inventive composition is absorbed into the patient's disordered tissue. The patient's disordered tissue is estimated to have an area of about 0.5 cm$^2$. The patient's disordered tissue is then examined after about one hour and is found to have reduced redness, which is however not as reduced compared to that achieved in Example 1. Similarly, the eosinophil assay is increased but not to the extent of that in Example 1 which used benzalkonium chloride.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of treating a cold sore comprising:
   identifying a cold sore treatment site;
   obtaining an applicator which holds a treatment composition for application to and penetration into the cold sore treatment site, wherein the treatment composition includes an anti-infective agent in a carrier, wherein the treatment composition is a liquid and has a viscosity that enhances rapid absorption into the cold sore treatment site without remaining on the cold sore treatment site for extended time periods;
   vigorously agitating the cold sore treatment site with the applicator in a manner such that the treatment composition is simultaneously delivered as the cold sore treatment site is agitated to enhance penetration of the treatment composition into the cold sore treatment site; and
   allowing the treatment composition to penetrate into the cold sore treatment site so that the composition is no longer visibly detectable on the cold sore treatment site within several minutes after delivery of the treatment composition onto the cold sore treatment site.

2. A method as recited in claim 1, wherein the anti-infective agent is an organochloride.

3. A method as recited in claim 1, wherein the anti-infective agent is benzalkonium chloride.

4. A method as recited in claim 1, wherein the anti-infective agent is benzalkonium chloride in an amount ranging from about 0.01% to about 0.5% by volume of the treatment composition.

5. A method as recited in claim 1, wherein the anti-infective agent is selected from the group consisting of benzalkonium bromide and cetyl trimethylammonium bromide.

6. A method as recited in claim 1, wherein the anti-infective agent is selected from the group consisting of benzethonium chloride, methyl benzethonium chloride, cetyl pyridinium chloride, chloroxylenol, hexachlorophene, triclosan, and chlorhexidine.

7. A method as recited in claim 1, wherein the anti-infective agent is at least one quaternary ammonium chloride having 6–18 carbons.

8. A method as recited in claim 1, wherein the carrier includes isopropyl alcohol.

9. A method as recited in claim 1, wherein the carrier includes isopropyl alcohol and water.

10. A method as recited in claim 1, wherein the carrier comprises isopropyl alcohol and water, wherein the water is included in an amount of about 30% by volume of the carrier and wherein the isopropyl alcohol is included in an amount of about 70% by volume of the carrier.

11. A method as recited in claim 1, wherein the organohalide includes benzalkonium chloride in an amount ranging from 0.01% to about 0.5% by volume of the treatment composition, wherein the carrier includes water in an amount of about 30% by volume of the carrier and wherein the carrier includes isopropyl alcohol in an amount of about 70% by volume of the carrier.

12. A method as recited in claim 1, wherein the carrier comprises an alcohol selected from the group consisting of ethanol, methanol, cetyl alcohol, benzyl alcohol and combinations thereof.

13. A method as recited in claim 1, wherein the carrier comprises an acetic compound selected from the group consisting of acetone, acetic acid, acetic anhydride, and mixtures thereof.

14. A method as recited in claim 1, wherein the treatment composition is void of penetration inhibiting components.

15. A method as recited in claim 1, wherein the cold sore treatment site is vigorously agitated by applying significant pressure to the cold sore treatment site.

16. A method as recited in claim 1, wherein the cold sore treatment site is vigorously agitated by rubbing the cold sore treatment site.

17. A method as recited in claim 1, wherein the cold sore treatment site is vigorously agitated by simultaneously applying significant pressure to the cold sore treatment site and rubbing the cold sore treatment site with the delivery and agitation means.

18. A method as recited in claim 1, further comprising applying a topical anesthetic to the cold sore treatment site.

19. A method of treating a cold sore comprising:
   identifying a cold sore treatment site;
   obtaining an applicator which contains a treatment composition,
      wherein the applicator includes
         delivery and agitation means for delivering the treatment composition and for agitating the cold sore treatment site, and
         means for supporting the delivery means
      wherein the treatment composition includes an organohalide in a carrier, wherein the treatment composition is a liquid and has a viscosity that enhances rapid absorption into the cold sore treatment site without remaining on the cold sore treatment site for extended time periods;
   vigorously agitating the cold sore treatment site with the applicator in a manner such that the treatment composition is simultaneously delivered as the cold sore treatment site is agitated to enhance penetration of the treatment composition into the cold sore treatment site; and
   allowing the treatment composition to penetrate into the cold sore treatment site so that the composition is no longer visibly detectable on the cold sore treatment site within several minutes after delivery of the treatment composition onto the cold sore treatment site.

20. A method as recited in claim 19, wherein the organohalide is benzalkonium chloride.

21. A method as recited in claim 19, wherein the carrier includes isopropyl alcohol.

22. A method as recited in claim 19, wherein the carrier includes isopropyl alcohol and water.

23. A method as recited in claim 19, wherein the carrier comprises isopropyl alcohol and water, wherein the water is included in an amount of about 30% by volume of the carrier and wherein the isopropyl alcohol is included in an amount of about 70% by volume of the carrier.

24. A method as recited in claim 19, wherein the organohalide includes benzalkonium chloride in an amount ranging from 0.01% to about 0.5% by volume of the treatment composition, wherein the carrier includes water in an amount of about 30% by volume of the carrier and wherein the carrier includes isopropyl alcohol in an amount of about 70% by volume of the carrier.

25. A method as recited in claim 19, wherein the treatment composition is void of penetration inhibiting components.

26. A method as recited in claim 19, wherein the cold sore treatment site is vigorously agitated by applying significant pressure to the cold sore treatment site.

27. A method as recited in claim 19, wherein the cold sore treatment site is vigorously agitated by rubbing the cold treatment site.

28. A method as recited in claim 19, wherein the cold sore treatment site is vigorously agitated by simultaneously applying significant pressure to the cold sore treatment site and rubbing the cold sore treatment site with the delivery and agitation means.

29. A method of treating a cold sore comprising:
   identifying a cold sore treatment site;
   obtaining an applicator which contains a treatment composition,
      wherein the applicator includes
         delivery and agitation means for delivering the treatment composition and for agitating the cold sore treatment site,
         means for supporting the delivery means, and
         reservoir means for containing the treatment composition;
      wherein the treatment composition includes an organohalide in a carrier, wherein the treatment composition is a liquid and has a viscosity that enhances rapid absorption into the cold sore treatment site without remaining on the cold sore treatment site for extended time periods;
   vigorously agitating the cold sore treatment site with the applicator in a manner such that the treatment composition is simultaneously delivered as the cold sore treatment site is agitated to enhance penetration of the treatment composition into the cold sore treatment site; and
   allowing the treatment composition to penetrate into the cold sore treatment site so that the composition is no longer visibly detectable on the cold sore treatment site within 2 minutes after delivery of the treatment composition onto the cold sore treatment site.

30. A method of treating a cold sore comprising:

identifying a cold sore treatment site;

obtaining an applicator which contains a treatment composition,
   wherein the applicator includes
      delivery and agitation means for delivering the treatment composition and for agitating the cold sore treatment site,
      means for supporting the delivery means, and
      reservoir means for containing the treatment composition and for providing fluid communication with the delivery and agitation means when use of the applicator is desired for application of the treatment composition;
   wherein the treatment composition includes an organohalide in a carrier, wherein the treatment composition is a liquid and has a viscosity that enhances rapid absorption into the cold sore treatment site without remaining on the cold sore treatment site for extended time periods;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within 2 minutes after delivery of the treatment composition onto the cold sore treatment site.

31. A method of treating a cold sore comprising:

identifying a cold sore treatment site;

obtaining an applicator which contains a treatment composition,
   wherein the applicator includes
      delivery and agitation means for delivering the treatment composition and for agitating the cold sore treatment site,
      means for supporting the delivery means, and
      reservoir means for containing the treatment composition and for providing continual fluid communication with the delivery and agitation means until all of the treatment composition held in the reservoir means has been delivered to the delivery and agitation means;
   wherein the treatment composition includes an organohalide in a carrier, wherein the treatment composition is a liquid and has a viscosity that enhances rapid absorption into the cold sore treatment site without remaining on the cold sore treatment site for extended time periods;

rupturing the reservoir means to enable the treatment composition to be delivered to the delivery and agitation means;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within 2 minutes after delivery of the treatment composition onto the cold sore treatment site.

32. A method of treating a cold sore comprising:

identifying a cold sore treatment site;

obtaining an applicator which holds a treatment composition for application to and penetration into the cold sore treatment site, wherein the treatment composition includes an anti-infective agent in a carrier, wherein the treatment composition is a liquid and has a viscosity that enhances rapid absorption into the cold sore treatment site without remaining on the cold sore treatment site for extended time periods, wherein the treatment composition is substantially oil free;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within several minutes after delivery of the treatment composition onto the cold sore treatment site.

33. A method as recited in claim 32, wherein the treatment composition is void of penetration inhibiting components.

34. A method as recited in claim 32, wherein the cold sore treatment site is vigorously agitated by applying significant pressure to the cold sore treatment site.

35. A method as recited in claim 32, wherein the cold sore treatment site is vigorously agitated by rubbing the cold sore treatment site.

36. A method of treating a cold sore comprising:

identifying a cold sore treatment site;

obtaining an applicator which holds a treatment composition for application to and penetration into the cold sore treatment site, wherein the treatment composition includes an organohalide in a carrier, wherein the carrier includes isopropyl alcohol, wherein the treatment composition is a liquid and has a viscosity that enhances rapid absorption into the cold sore treatment site without remaining on the cold sore treatment site for extended time periods;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within several minutes after delivery of the treatment composition onto the cold sore treatment site.

37. A method as recited in claim 36, wherein the cold sore treatment site is vigorously agitated by applying significant pressure to the cold sore treatment site.

38. A method as recited in claim 36, wherein the cold sore treatment site is vigorously agitated by rubbing the cold sore treatment site.

39. A method as recited in claim 36, wherein the cold sore treatment site is vigorously agitated by simultaneously applying significant pressure to the cold sore treatment site and rubbing the cold sore treatment site with the delivery and agitation means.

40. A method of treating a cold sore comprising:

identifying a cold sore treatment site;

obtaining an applicator which holds a treatment composition for application to and penetration into the cold sore treatment site, wherein the treatment composition includes benzalkonium chloride in a carrier, wherein the treatment composition is a liquid and has a viscosity that enhances rapid absorption into the cold sore treatment site without remaining on the cold sore treatment site for extended time periods;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within several minutes after delivery of the treatment composition onto the cold sore treatment site.

41. A method as recited in claim 40, wherein the cold sore treatment site is vigorously agitated by applying significant pressure to the cold sore treatment site.

42. A method as recited in claim 40, wherein the cold sore treatment site is vigorously agitated by rubbing the cold sore treatment site.

43. A method of treating a cold sore comprising:

identifying a cold sore treatment site;

obtaining an applicator which holds a treatment composition for application to and penetration into the cold sore treatment site, wherein the treatment composition includes benzalkonium chloride in a carrier, wherein the carrier includes isopropyl alcohol, wherein the treatment composition is a liquid and has a viscosity that enhances rapid absorption into the cold sore treatment site without remaining on the cold sore treatment site for extended time periods;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within several minutes after delivery of the treatment composition onto the cold sore treatment site.

44. A method as recited in claim 43, wherein the cold sore treatment site is vigorously agitated by applying significant pressure to the cold sore treatment site.

45. A method as recited in claim 43, wherein the cold sore treatment site is vigorously agitated by rubbing the cold sore treatment site.

46. A method of treating a cold sore comprising:

identifying a cold sore treatment site;

obtaining an applicator which holds a treatment composition for application to and penetration into the cold sore treatment site, wherein the treatment composition includes benzalkonium chloride in a carrier, wherein the carrier includes isopropyl alcohol and water, wherein the treatment composition is a liquid and has a viscosity that enhances rapid absorption into the cold sore treatment site without remaining on the cold sore treatment site for extended time periods;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment-site within several minutes after delivery of the treatment composition onto the cold sore treatment site.

47. A method as recited in claim 46, wherein the cold sore treatment site is vigorously agitated by applying significant pressure to the cold sore treatment site.

48. A method as recited in claim 46, wherein the cold sore treatment site is vigorously agitated by rubbing the cold sore treatment site.

49. A method of treating a cold sore comprising:

identifying a cold sore treatment site;

obtaining an applicator which holds a treatment composition for application to and penetration into the cold sore treatment site, wherein the treatment composition includes benzalkonium chloride in a carrier, wherein the carrier is primarily isopropyl alcohol and includes water in an amount ranging from about 20% to about 40% by volume of the carrier;

vigorously agitating the cold sore treatment site with the applicator in a manner such that the treatment composition is simultaneously delivered as the cold sore treatment site is agitated to enhance penetration of the treatment composition into the cold sore treatment site; and allowing the treatment composition to penetrate into the cold sore treatment site so that the composition is no longer visibly detectable on the cold sore treatment site within several minutes after delivery of the treatment composition onto the cold sore treatment site.

50. A method as recited in claim 49, wherein the cold sore treatment site is vigorously agitated by applying significant pressure to the cold sore treatment site.

51. A method as recited in claim 49, wherein the cold sore treatment site is vigorously agitated by rubbing the cold sore treatment site.

* * * * *

UNITED STATES PATENT AND TRADEMARK OFFICE
CERTIFICATE OF CORRECTION

PATENT NO.    : 6,211,243 B1
DATED         : April 3, 2001
INVENTOR(S)   : B. Ron Johnson It is certified that error appears in the above-identified patent and that said Letters Patent is hereby corrected as shown below:

Column 3,
Line 24, after "stopped" change "in" to -- when --
Line 37, after "conventional" insert -- compositions. --

Column 6,
Line 21, after "through either" change "apply" to -- applying --

Column 10,
Line 66, after "also" change "act" to -- acts --

Column 11,
Line 4, before "water" change "above" to -- above, --

Column 12,
Line 45, after "achieved" change "though" to -- through --

Column 13,
Line 46, after "mucous membranes" change "an" to -- and --

Column 16,
Line 20, before "polyester" insert -- as --
Line 23, after "tend" insert -- to --
Line 37, before "manner" insert -- a --

Column 19,
Line 52, after "typically" delete "are"
Line 64, before "the moisture" change "concentration" to -- concentrate --

Column 21,
Line 39, before "the treatment" change "bold" to -- hold --

Column 29,
Line 22, after "treatment" change "compostion" to -- composition --

UNITED STATES PATENT AND TRADEMARK OFFICE
CERTIFICATE OF CORRECTION

PATENT NO.    : 6,211,243 B1
DATED         : April 3, 2001
INVENTOR(S)   : B. Ron Johnson It is certified that error appears in the above-identified patent and that said Letters Patent is hereby corrected as shown below:

<u>Column 34,</u>
Line 36, after "cold" insert -- sore --

<u>Column 38,</u>
Line 20, after "cold sore" change "treatment-site" to -- treatment site --

Signed and Sealed this

Thirteenth Day of August, 2002

Attest:

JAMES E. ROGAN
*Attesting Officer*    *Director of the United States Patent and Trademark Office*